US005837470A

United States Patent [19]
Carlson et al.

[11] Patent Number: 5,837,470
[45] Date of Patent: Nov. 17, 1998

[54] METHOD OF RECOVERING A BIOLOGICAL MOLECULE FROM A RECOMBINANT MICROORGANISM

[75] Inventors: Peter S. Carlson, Alexandria; Ernesto J. Quintero, McLean, both of Va.; David M. Manyak, Ellicott City; Alan B. Chmurny, Frederick, both of Md.

[73] Assignee: Oceanix Biosciences Corporation, Hanover, Md.

[21] Appl. No.: 21,984

[22] Filed: Feb. 11, 1998

Related U.S. Application Data

[62] Division of Ser. No. 766,308, Dec. 13, 1996.

[60] Provisional application No. 60/008,682 Dec. 15, 1995.

[51] Int. Cl.$^6$ .............................. C12Q 1/68; C12P 21/02
[52] U.S. Cl. ...................... 435/6; 435/69.1; 435/172.3; 435/172.2; 435/252.3
[58] Field of Search .......................... 435/6, 69.1, 172.2, 435/172.3, 252.3

[56] References Cited

FOREIGN PATENT DOCUMENTS

| 0 061 253 | 9/1982 | European Pat. Off. |
| 0 133 046A | 2/1985 | European Pat. Off. |
| WO 94 20604A | 9/1994 | European Pat. Off. |
| 1 602 074 | 11/1981 | United Kingdom . |

OTHER PUBLICATIONS

Matsushima, P. et al., Protoplast Fusion. In A.L. Demain and N.A. Solomon, eds. Manual of Industrial Microbiology and Biotechnology. American Society for Microbiology, Washington, D.C. pp. 170–183.(1986).

Hopwood, D.A., "Genetic Studies With Bacterial Protoplasts", *Ann. Rev. Microbiol.*, vol. 35, pp. 237–272 (1981).

Mirdamadi–Tehrani, J. et al., "Genetic Analysis of Intraspecies Recombinant Formation by Protoplast Fusion with Three Species of Streptomyces", *FEMS Microbiology Letters*, vol. 36, pp. 299–302 (1986).

Chen, W. et al., "Intergeneric Protoplast Fusion Between *Ruminococcus albus* and an Anaerobic Recombinant, FE7", *Applied and Environmental Microbiology*, vol. 54, pp. 1249–1253 (1988).

Aono, R. et al., "Genetic Recombination After Cell Fusion of Protoplasts From the Facultative Alkaliphile Bacillus sp. C–125", *Microbiology*, vol. 40, pp. 3085–3090 (1994).

Rajendran, N., "Expression of the Insecticidal Crystal Protein Gene From a Gram–Positive *Bacillus thuringiensis* in a Gram–Negative *Pseudomonas fluorescens* Mediated by Protoplast Fusion", *FEMS Microbiology Letters*, vol. 122, pp. 103–108 (1994).

Prakash, R.K. et al., "Creation of Novel Nitrogen–Fixing Actinomycetes by Protoplast Fusion of Frankia With Streptomyces", *Plant Molecular Biology*, vol. 10, pp. 281–289 (1988).

Kinashi, H. et al., "Isolation and Characterization of Linear Plasmids From Lankacidin–Producing Streptomyces Species", *The Journal of Antibiotics*, vol. 47, pp. 1447–1455 (1994).

Yamashita, F. et al. "New Antibiotic–Producing Streptomycetes, Selected by Antibiotic Resistance as a Marker", *The Journal of Antibiotics*, vol. 38, pp. 58–63 (1985).

Ikeda, Il., "Genetic Engineering of Antibiotic–Producing Microogranisms", In S. Omura, ed., The Search for Bioactive Compounds from Microorganisms. Springer–Verlag, New York, pp. 327–336.

New, R.R.C., ed. Liposomes, A Practical Approach, IRI, Press New York.

Smith, J.G. et al., "Liposomes as Agents of DNA Transfer", *Biochimica et Biophysica Acta*, vol. 1154, pp. 327–340 (1993).

Nabel, G.J. et al., "Direct Gene Transfer With DNA–Liposome Complexes in Melanoma: Expression, Biologic Activity, and Lack of Toxicity in Humans", *Proc. Natl. Acad. Sci.*, vol. 90, pp. 11307–11311 (1993).

Goyal, K. et al., "Gene Therapy Using DC–Chol Liposomes", *J. Liposome Res.*, vol. 5, pp. 49–60 (1995).

Bakker–Woudenberg, I.A.J.M. et al., "Efficacy of Gentamicin or Ceftazidime Entrapped in Liposomes With Prolonged Blood Circulation and Enhanced Localization in *Klebsiella pneumoniae*–Infected Lung Tissue", *J. Infect. Dis.*, vol. 171, pp. 938–947 (1995).

Bermudez, L.E. et al., "Treatment of Disseminated Mycobacterium Avium Complex Infection of Beige Mice With Liposome–Encapsulated Aminoglycosides", J. Infec. Dis. 16:1262–1267 (1990).

Boizet, B. et al., "Transfection of *Lactobacillus bulgaricus* Protoplasts by Bacteriophage DNA", *Applied and Environmental Microbiology*, vol. 54, pp. 3014–3018 (1988).

Chernyavskii, V.A. et al., "Transfection of *Escherichia coli* Spheroplasts by Phage DNA Encapsulated in Lipids", *Biotekhnologiya*, vol. 2, pp. 23–27 (1986).

Lampel, J.S. et al., "Transformation and Transfection of Anthracycline–Producing Streptomycetes", *Appl. Environ. Microbiol.*, vol. 51, pp. 126–131 (1986).

(List continued on next page.)

*Primary Examiner*—James Ketter
*Attorney, Agent, or Firm*—Finnegan, Henderson, Farabow, Garrett & Dunner, L.L.P.

[57] ABSTRACT

The present invention is directed to a method of recovering a biological molecule from a recombinant microorganism produced using a method based on either protoplast fusion or lipofection. The present invention further provides a method of identifying, isolating, or making a biological molecule from a recombinant microorganism and also encompasses the biological molecule produced by a recombinant microorganism. Moreover, the present invention relates to a method of making a recombinant microorganism containing the nucleic acid of a microorganism in an environmental sample, as well as the recombinant microorganisms themselves. Finally, the present invention is directed to a method of making a recombinant library, as well as the recombinant library itself.

14 Claims, 7 Drawing Sheets

OTHER PUBLICATIONS

Holubova, I. et al., "Transfer of Liposome–Encapsulated Plasmid DNA to *Bacillus subtilis* Protoplasts and Calcium–Treated *Escherichia coli* Cells", *Folia Microbiol.*, vol. 30, pp. 97–100 (1985).

Makins, J.F. et al., "Liposome–Mediated Transformation of Streptomycetes by Chromosomal DNA". Nature 293:671–673 (1981).

McInerney, J.O., "Extraction of Prokaryotic Genomic DNA From Marine Microbial Communities Suitable For Amplification Using The Polymerase Chain Reaction", Int. Revue ges. Hydrobiol., vol. 80, pp. 351–360 (1995).

Frischer, M.E., et al., "Plasmid Transfer to Indigemous Marine Bacterial Population by Natural Transformation", FEMS Microbiology Ecology, vol. 15, pp. 127–136 (1994).

Lovell, C.R. et al., "Purification of DNA From Estuarine Sediments", *Journal of Microbiology Methods,* vol. 20, pp. 161–174 (1994).

Stein, J.L. et al., "Characterization of Uncultivated Prokaryotes: Isolation and Analysis of a 40–Kilobase–Pair Genome Fragment From a Planktonic Marine Archaeon", *Journal of Bacteriology,* vol. 178, pp. 591–599 (1996).

Van Der Vossen, Jos. M.B.M. et al., "Liposome–enhanced transformation of Streptococcus lactis and plasmid transfer by intergenic protoplast fusion of Streptococcus lactis and Bacillus subtilis", *FEMS Microbiology Letters,* vol. 49, pp. 323–329 (1988).

METHOD OF RECOVERING A BIOLOGICAL MOLECULE FROM A RECOMBINANT MICROORGANISM

CROSS REFERENCE TO RELATED APPLICATIONS

This is a division of application Ser. No. 08/766,308, filed Dec. 13, 1996, and claims the benefit of U.S. provisional application Ser. No. 60/008,682, filed Dec. 15, 1995, all of which are incorporated herein by reference.

FIELD OF THE INVENTION

The present invention relates to recovering a biological molecule from a recombinant microorganism using an environmental sample.

BACKGROUND OF THE INVENTION

In the early 1980's, as traditional sources of natural products began yielding fewer novel pharmaceutical molecules, and the developing science of molecular biology appeared to offer more direct and expedient methods of drug development, interest in the pharmaceutical industry shifted away from natural products and toward developing protein-based therapies for treating human disease. However, limitations of protein-based drugs included high costs to produce, limited stability once isolated, and required delivery via injection.

During this same period, advances in understanding molecular mechanisms of diseases allowed the evaluation of hundreds of new compounds for pharmacological activity. Methods of evaluation include recreating a course of treatment of a particular disease in a test-tube, or by using receptor/ligand or enzyme/substrate assays. These advances, and the information these assays provided, have revolutionized pharmaceutical development.

Even with the extensive screening of new compounds, however, the productivity of drug discovery research within the pharmaceutical industry has declined while the costs of pharmaceutical R&D have continued to rise. The rising costs associated with successful drug development is partly due to large number of drug failures. Thus, to counteract these rising costs, new drugs need to be discovered cheaply and efficiently. One potential source of new drugs exists in environmental samples.

Even small environmental samples contain an enormous number and variety of microorganisms. For instance, marine bacteria can be found in dense concentrations of up to $1 \times 10^6$ cells per milliliter (ml) of sea water, and $5 \times 10^{10}$ cells per gram of dry weight sediment. Unfortunately, microorganisms living in environmental samples are, for the most part, uncharacterized and undiscovered. If characterized, these microorganisms potentially contain biological molecules, such as genetic material, gene products, and secondary metabolites, that may provide treatments for diseases or cancer, as well as applications in commercial industries. Thus, environmental samples containing microorganisms represent a promising source of biologically active natural products.

Nonetheless, a major, limiting constraint in utilizing environmental samples as a source of new products is that less than 1% of the microorganisms found in the environment can be cultured using existing fermentation protocols and growth media formulations. (1, 2, 3) The inability to culture the remaining 99% may be due to the microorganisms in environmental samples existing in a "viable but non-culturable state" or to the absence of specific growth factors or nutrients in culture media. As a result, during standard isolation, culturing, and screening protocols, most environmental microorganisms fail to reproduce and, therefore, are lost. Clearly, the inability to culture environmental microorganisms prevents the identification of new biologically active, natural products.

Recent reports discuss the recovery of DNA from environmental samples. (4) One report describes the isolation of DNA from uncultured bacteria found in seawater and/or marine sediments, and then the cloning of the isolated DNA into a vector. (5) The process of cloning is a generic term that describes the insertion of a nucleic acid fragment into a vehicle, allowing for the continued production of the inserted fragment. This vehicle is generally called a vector.

The work in a second report discussing the recovery of DNA from environmental samples relies on a polymerase chain reaction (PCR) to amplify DNA fragments, previously isolated from uncultured bacteria. The PCR amplified fragments are then cloned into a vector, just as in the first report. (6) Although potentially useful, several obstacles are encountered with both of these approaches.

There exists numerous problems with the cloning of nucleic acid into a vector. First, only nucleic acid fragments of a size less than 50 kb can be successfully inserted into a vector. However, many genes, and clusters of genes required for biosynthesis of biological molecules, span regions in genomic DNA greater than 50 kb. Because of the size constraints of vectors, these large genes, and gene clusters, would rarely be recovered after cloning.

Similarly, many proteins involved in a particular synthetic pathway are often encoded by genes linearly arranged in the genome, spanning regions greater than 50 kb. (7) For instance, antibiotic-producing strains of bacteria show self resistance to their own antibiotics. It is thought that the expression of resistance genes is synchronized with that of antibiotic biosynthesis, and that the genes responsible for antibiotic resistance are located close to the biosynthetic genes. (8) If the antibiotic resistance and biosynthetic genes span a region in the genome greater than 50 kb, utilizing vectors as a method of recovering nucleic acid would preclude the cloning of these synthetic pathways.

Second, to decrease the size of nucleic acid fragments inserted into a vector, the isolated nucleic acid is digested with a restriction endonuclease (RE), an enzyme that cuts the nucleic acid at specific sequences. Evidence exists that environmental microorganisms, such as marine bacteria, have evolved systems, called RE/methylation systems, that prohibit the digesting of nucleic acid by sterically blocking the restriction enzyme from the nucleic acid. (9) This blocking of restriction enzyme digestion defeats any attempt at inserting smaller nucleic acid fragments into the vector.

The third obstacle associated with cloning nucleic acid into a vector involves the large amount of nucleic acid lost during each cloning step performed. By losing nucleic acid, small restriction fragments and DNA sequences, existing as single copies in the genome, become underrepresented in the recovered clones.

Similarly, using PCR to clone nucleic acid also has its problems. PCR technology is an efficient method of amplifying small amounts of nucleic acid from a sample. Although a useful tool, PCR has limitations. Only fragments of a size less than 40 kb can be effectively amplified. Thus, an even greater size constraint exists for PCR reactions than is characteristic of direct cloning of nucleic acid into vectors.

A second problem associated with using PCR to clone nucleic acid is the potential presence of contaminating sequences in the sample, as well as in all stock solutions. If these contaminating sequences are amplified and then cloned, recovery of unwanted nucleic acid sequences occurs.

Finally, PCR reactions require short sequences of 10–20 base pairs (bp), called primers. To amplify specific target areas of a nucleic acid, the sequence of these primers must be known. Using specific, known primers limits the ability to amplify unknown nucleic acid sequences, resulting in a decrease in the heterogeneity and the randomness of the recovered sequences.

In light of the inability of available technology to access a biological molecule contained in and produced by the vast majority of the microbial world from unenriched environmental samples, Applicants have developed the technology described in the current invention.

SUMMARY OF THE INVENTION

Accordingly, the present invention is directed to a method of recovering a biological molecule from a recombinant microorganism, that substantially obviates one or more of the problems due to the limitations and disadvantages of the related art. The present invention further provides a method of identifying, isolating, or making a biological molecule from a recombinant microorganism and also encompasses the biological molecule produced by a recombinant microorganism. Moreover, the present invention relates to a method of making a recombinant microorganism containing the nucleic acid of a microorganism in an environmental sample, as well as the recombinant microorganisms themselves. Finally, the present invention is directed to a method of making a recombinant library, as well as the recombinant library itself.

Additional features and advantages of the invention will be set forth in the description which follows, and in part will be apparent from the description, or may be learned by practice of the invention. The objectives and other advantages of the invention will be realized and attained by the method and composition of matter particularly pointed out in the written description and claims hereof, as well as the appended drawings.

In one broad aspect, the invention relates to a biological molecule from a recombinant microorganism, wherein an environmental sample having microorganisms is obtained and the nucleic acid from the microorganisms is isolated and inserted into donor liposomes. The donor liposomes are then fused with recipient protoplasts to produce a recombinant microorganism. Culturing the recombinant microorganism results in the production of a biological molecule. In one specific aspect, the biological molecule is recovered. In another specific aspect, the biological molecule is identified, and still another specific aspect, the biological molecule is isolated.

In a second broad aspect, the invention relates to a biological molecule from a recombinant microorganism, wherein an environmental sample having microorganisms is obtained. Donor protoplasts are prepared from the environmental sample and fused with recipient protoplasts to produce a recombinant microorganism. Culturing the recombinant microorganism results in the production of a biological molecule. In one specific aspect of the present invention, the biological molecule is recovered. In another specific aspect, the biological molecule is identified, and still another specific aspect, the biological molecule is isolated.

In a further aspect, the present invention relates to a recombinant microorganism produced by either method, as well as a recombinant library made by combining recombinant microorganisms.

In yet another aspect, the present invention relates to making a biological molecule, wherein genetic material is identified and isolated using a recombinant microorganism produced by either method. This genetic material is cloned into a vector and cells are transformed with the vector. After culturing, a biological molecule is produced.

It is to be understood that both the foregoing general description and the following detailed description are exemplary and explanatory and are intended to provide further explanation of the invention as claimed.

The accompanying drawings are included to provide a further understanding of the invention, and are incorporated in and constitute a part of the specification, in order to explain the principles of the invention, but do not limit the invention.

DETAILED DESCRIPTION

Figure 1:
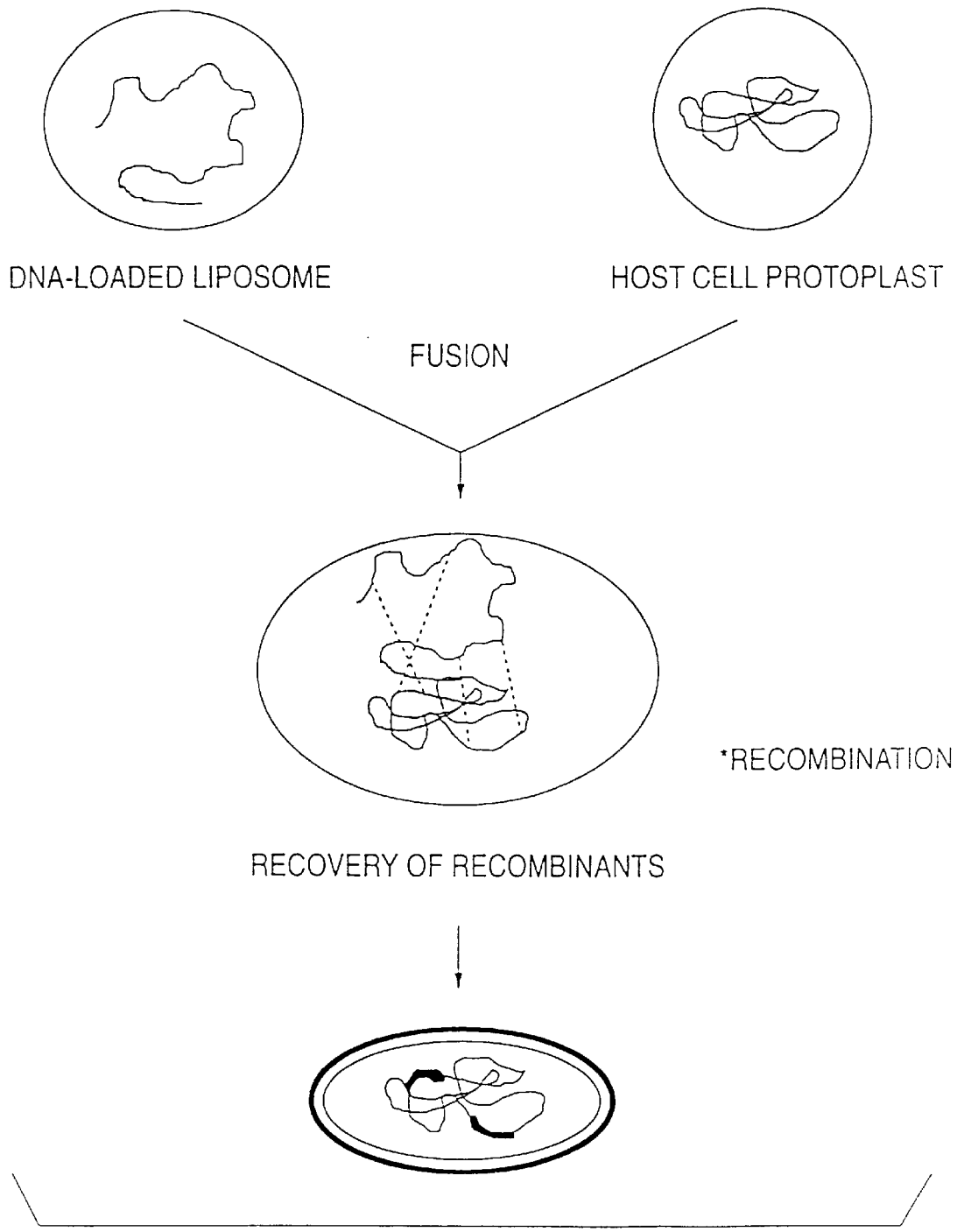
FIG. 1: Diagram of lipofection-based nucleic acid transfer.

The amount of money spent on research and development for new drugs continues to grow. U.S. based drug companies spend nearly fifteen billion dollars annually on product development; roughly 20 times the R&D spending in the early 1970's. Despite this phenomenal investment, the productivity of drug discovery research has sharply declined. One reason for the declining productivity of pharmaceutical R&D is the lack of uniqueness in the source of compounds being used for drug discovery. Fewer novel molecules with pharmaceutical activity are discovered because of exploitation of existing chemical and natural product libraries.

One recent approach to creating a highly diverse chemical library is through combinatorial chemistry. This process creates many derivatized structures from a given chemical backbone. Through different combinations of various chemical groups, a collection, or library, containing 100,000–1,000,000 independent compounds can be generated. Although promising, this approach requires prior knowledge of the chemical structure of the backbone.

Given the wide biodiversity of environmental microorganisms, the unique chemistries evolved by such microorganisms in response to hostile surroundings, and the growing examples of medicinally relevant activities in environmental extracts, Applicants believe environmental microorganisms are a promising source of novel bioactive natural products.

However, techniques typically used to characterize microorganisms obtained from an environmental sample first require enrichment of the microorganisms. Enrichment procedures usually involve culturing the microorganisms under standard laboratory conditions. Unfortunately, almost 99% of the microorganisms obtained from a an environmental sample do not survive these standard culturing procedures, either from the lack of required growth factors or nutrients in the culture media, or the inability of the microorganism to be cultured. Thus, the vast majority of microorganisms in an environmental sample remain unculturable, and thereby uncharacterized.

Rather than trying to identify, and then attempting to replicate, the conditions under which the nonculturable microorganisms can be grown, Applicants have developed a novel method that allows for the recovery of a biological molecule from a recombinant microorganism. In contrast to the standard procedures used for creating recombinant cells, the present invention eliminates the enrichment step, by not cell-culturing the environmental sample prior to producing recombinant microorganisms. Thus, the present invention enables the study and characterization of unculturable microorganisms obtained from environmental samples.

The claimed invention relates to a method of recovering a biological molecule from a recombinant microorganism, wherein the method comprises obtaining an environmental sample having microorganisms. This novel approach in recovering a biological molecule is termed "Combinatorial Genomics."

Combinatorial Genomics accesses both the natural products produced by environmental microorganisms and generates unique combinations of chemical structures by using recombinant microorganisms. Three types of recombinant a microorganisms can be produced by Combinatorial Genomics:

Type 1: A recombinant microorganism containing an intact section of genetic material from a donor microorganism encoding a molecule normally produced by the donor microorganism. This recombinant microorganism now produces the molecule normally found in the donor microorganism; or Type 2: A recombinant microorganism containing genetic material from a donor microorganism. During recombination, this material has rearranged with the recipient genome, producing a new, hybrid gene or altered cluster of genes. The product of this new hybrid gene or gene clusters is produced by the recombinant microorganism; or Type 3: Little or no genetic material from the donor microorganism is successfully transferred, and the resultant cell is identical to the starting recipient cell.

In type 1, one or more natural molecules from the otherwise unaccessible non-culturable microorganism are recovered, and in type 2, an entirely new molecule, or unnatural natural product, is recovered. In type 3, the resulting cell will be lost by proper selection parameters. Thus, by using Combinatorial Genomics, one environmental sample can yield hundreds, or thousands, of different recombinant microorganisms, each recombinant microorganism potentially producing an independent and unique molecule.

Therefore, Combinatorial Genomics can be viewed as a powerful method to produce new molecular structures from a previously unaccessible source. This technology could be considered the biological counterpart to combinatorial chemistry. However, unlike combinatorial chemistry, in which a known chemical backbone is required, Combinatorial Genomics creates novel products by relying on genetic recombination.

In the present invention, environmental samples are defined as crude, unenriched samples obtained from nature that contain microorganisms. These environmental samples are preferably uncultured. Examples include, but are not limited to, bodies of water, such as rivers, streams, lakes, and rain puddles. In a preferred embodiment, the body of water is an ocean. Examples of environmental samples also include soil, sediments associated with bodies of water, and air samples. Furthermore, environmental samples include microorganisms that are either living in, or living on, multicellular organisms. Types of multicellular organisms are well known in the art and include aquatic life, such as fish, sea sponges, whales, and terrestrial organisms, such as birds, reptiles, and mammals, including humans. Methods of obtaining environmental samples are well known in the art and therefore will not be detailed in the present invention.

In the present invention, microorganisms in an environmental sample include prokaryotes, such as Archaea and bacteria, and simple eukaryotes, such as fungi. In a preferred embodiment, the bacteria are either $Gram^+$ or $Gram^-$. As is well recognized in the art, $Gram^+$ bacteria are characterized by the lack of a peptidoglycan cell wall, while $Gram^-$ bacteria have such a cell wall.

Marine microorganisms represent an emerging and promising source for drug discovery, given the enormous diversity and well-documented use of molecules as a means of defense, communication, and competition. Marine microorganisms include the following general groups: bacteria, Archaea, fungi, microalgae, and phytoplankton.

Many of these marine microorganisms communicate via small molecules that are released into the water. These marine microorganisms also secrete chemicals for defensive purposes or to compete for space. Thus, Applicants believe that marine microorganisms should be a rich source of unique, small molecules with potential pharmacological activity.

In addition to small molecules, marine microorganisms also produce a variety of large molecules, including protein-based enzymes, which act as catalysts for biochemical reactions and polysaccharide-based biomaterials. Many of these marine biomaterials and enzymes have unique and commercially valuable properties as a result of the unusual physical, chemical, and biological conditions of the marine environments.

Examples of biomaterials already harvested from the sea include agar, carrageenan, and alginate, all of which are polysaccharide-based, gel-like materials obtained from seaweeds. Agar is used extensively as a support medium for culturing microorganisms and medical diagnostic applications. Carrageenan and alginate are used as thickening agents in foods and consumer products.

Similarly, many enzymes now used for industrial purposes are derived from environmental microorganisms. Categories of enzymes and their commercial uses include (1) protein-degrading enzymes (proteases) for detergents, processing leather, and food processing, (2) carbohydrate-converting enzymes (carbohydrases) for cleaning, food processing, and sweetener production, (3) fat-degrading enzymes (lipases) for detergents and cheese production, and (4) a variety of specialized enzymes for use in biomedical products and reagents, bioremediation, synthesis of pharmaceuticals, and diagnostics.

New applications based on enzymes with unusual properties can create niche market opportunities and expand the overall enzyme market. One example of a relatively new commercial product, developed by the biotechnology company Cetus, is a thermostable DNA polymerase, an enzyme that does not degrade at high-temperatures. This enzyme is an important component of the polymerase chain reaction (PCR) used for analysis of DNA, gene cloning, DNA fingerprinting, and diagnosis of hereditary disease. Thermostable DNA polymerase was originally obtained from a microbe living in geothermal springs. Later varieties include thermostable DNA polymerases from deep-sea thermal vent microbes.

Thus, obtaining environmental samples from extreme environments, such as deep sea thermal vents, methane/hydrocarbon seeps, polar waters, and brine pools, represent a promising source of biological molecules and are contemplated by the present invention.

In a preferred embodiment, the microorganisms include the marine archaebacteria, or Archaea. These microorganisms inhabit the effluent water from deep-sea thermal vents, which are essentially volcanoes that arise from the ocean floor. Archaea can live in this vent environment at water temperatures exceeding 100° C., along with extreme hydrostatic pressures. Furthermore, the chemistry of these vents is extremely unusual, with the water containing high concentrations of metals, salts, and organic molecules.

These microbes (called "hyperthermophiles") are a potential source of unique biological molecules. Because these Archaea live in water temperatures near 100° C., the cellular enzymes are optimally adapted to these ambient temperatures, and therefore, extremely thermostable. Similarly, these microorganisms can metabolize sulfur, methane, and other molecules. Thus, because of the unusual chemistries at the vents. Applicants believe that Archaea should contain enzymes and small molecules with novel activities and specificities.

Using this same reasoning, other microorganisms living in frigid environments, such as Antarctic ice shelves or hydrocarbon-laden cold-water seeps, are also contemplated by the present invention. Thus, Applicants also contemplate that microorganisms living in these environmental samples should be a rich source of biological molecules.

In the present invention, biological molecules are molecules produced by the recombinant microorganisms of the invention. In a preferred embodiment, a biological molecule includes genetic material, a gene product, or a secondary metabolite, as defined below. In a further preferred embodiment, a biological molecule may be produced naturally in the microorganisms in the environmental sample or may be new molecules generated by genetic recombination, as described below.

In the present invention, genetic material is defined as both deoxyribonucleic acid (DNA), such as chromosomal or plasmid DNA, mitochondrial DNA, and ribonucleic acid (RNA). RNA includes both transfer RNA (tRNA) and messenger RNA (mRNA).

Similarly, the present invention defines nucleic acid as both DNA and RNA.

A gene product is defined in the present invention as both the RNA encoded by a gene, as well as the protein translated from the encoded RNA. Gene products encompass both a single gene product as well as an entire, multi-enzyme pathway.

A secondary metabolite is defined in the present invention as a direct or indirect byproduct generated by a reaction involving a gene product. Examples of secondary metabolites include small, low molecular weight compounds, such as beta-lactam antibiotics, dopamines, and cyclosporins.

It is specifically contemplated in the present invention that the terms biological molecule, genetic material, gene product, and secondary metabolite include both naturally occurring materials found in a microorganism living in an environmental sample, as well as recombinantly produced compounds. In other words, the present invention recognizes that the process of recombination of the environmental microorganisms' nucleic acid and the recipient genome generates new arrangements of nucleic acid by random insertion, not normally found in nature. Biological molecule, genetic material, gene product, and secondary metabolite are intended in the present invention to include the products of these new arrangements.

Thus, the present invention discloses a method of recovering, identifying, isolating, and producing a biological molecule from a recombinant microorganism by two basic methods. First, donor protoplasts prepared directly from an environmental sample, without prior culturing, are fused with recipient protoplasts, producing recombinant microorganisms. The second method isolates nucleic acid directly from an environmental sample, without prior culturing of the microorganisms. The isolated nucleic acid is encapsulated in donor liposomes and fused with recipient protoplasts, producing recombinant microorganisms.

Protoplast fusion is a versatile technique for facilitating gene transfer and genetic recombination among a variety of prokaryotic and eukaryotic microorganisms. In the present invention, a protoplast is defined as a microorganism lacking a coherent intact cell wall.

Unlike other methods of gene transfer, protoplast fusion does not use vectors, such as transducing phages, or require specific factors to transfer the vector into a competent host. However, protoplast fusion does require identification of the conditions needed to form stable protoplasts, to fuse the donor cell with the recipient protoplasts, and to regenerate viable cells from fused protoplasts. (10)

Protoplasts are prepared by removing the cell wall with lytic enzymes, in the presence of osmotic stabilizers, which prevents rupturing of the protoplasts. After protoplast formation, a chemical agent, such as polyethylene glycol (PEG), or a physical agent, such as an electric field, induces the protoplasts to fuse and form transient hybrids, or merodiploids, which are genetically unstable and undergo extensive genetic recombination, yielding numerous genetically diverse clonal cell lines.

During the hybrid state, the genomes of the donor and recipient protoplasts reassort and genetic recombination occurs. In the present invention, genetic recombination is defined as the insertion of nucleic acid, obtained from a microorganism in an environmental sample, into the genome of the recipient protoplast. A genome is defined in the present invention as the nucleic acid of a organism, including chromosomal DNA and mitochondrial DNA. For prokaryotes, genetic recombination occurs at very high frequencies because the prokaryotic chromosomes exist freely in the cytoplasm, in contrast to being contained in a nuclear membrane as found in eukaryotic cells. (10) Once genetic recombination occurs, viable cells are selected using techniques standard in the art.

Protoplast fusion has been used for the successful interspecies and intergenus transfer of genes between different strains of Gram$^+$ bacteria and between Gram$^+$ and Gram$^-$ bacteria. (11, 12, 13, 14) For example, an insecticide encoded by the crystal protein gene from *Bacillus thuringiensis* (Gram$^+$) was transferred by protoplast fusion into *Pseudomonas fluorescens* (Gram$^-$). (15) Similarly, the capacity to fix atmospheric nitrogen was conferred to *Streptomyces griseofuscus* by intergenus transfer of a large cluster of nif genes from Frankia via protoplast fusion. (16)

The transfer of bioactive metabolite production has also been accomplished using protoplast fusions. A plasmid containing genes encoding for antibiotic resistance was transferred to a non-antibiotic producing mutant of *Strepto-*

*myces rochei* by protoplast fusion. The resulting recombinant microorganism gained the ability to produce two different antibiotics, lankacidin and lankamycin. (17) Similarly, protoplast fusions between antibiotic producing strains of *Streptomyces* have been used to generate recombinants which produce novel antibiotic molecules. (18, 19)

The present invention also relies on liposomes to transfer the nucleic acid of a microorganism in an environmental sample into recipient protoplasts. Liposome mediated transfer, termed lipofection, transfers nucleic acids into cells with high efficiency. (20, 21) Applications of this procedure in eukaryotic cells include human clinical trials of gene therapy for treating cancer (melanomas) and cystic fibrosis. (22, 23) In prokaryotic cells, lipofection has delivered antimicrobial agents (24, 25), phage DNA (26, 27), plasmid DNA (28, 29), and chromosomal DNA (30) into recipient protoplasts.

Lipofection encapsulates isolated nucleic acid into a lipid "bubble," termed a liposome. In the present invention, these donor liposomes are then fused, with recipient protoplasts, producing transient hybrids or diploids. Viable cells that have undergone genetic recombination are then selected as above.

Historically, both protoplast fusion and lipofection have been limited to the transfer of nucleic acid from enriched populations of donor cells. Enrichment of donor cells is usually performed by culturing the donor cell prior to preparing donor protoplasts or donor liposomes. Efficient transformation of recipient protoplasts requires large quantities of donor protoplast or liposomes, and the purpose of enriching the donor cells was an attempt to overcome the inability of generating large quantities of protoplasts or liposomes without starting with high numbers of cells. Thus, by culturing cells prior to protoplast or liposome formation, successful transformation can occur.

In the present invention, both lipofection and protoplast fusion protocols differ from previously published strategies for transferring nucleic acid because: 1) both utilize unenriched environmental samples to obtain the nucleic acid from microorganisms, rather than from cultured stocks; 2) both do not require the cloning of the nucleic acid into a vector, alleviating the size constraints characteristic of vectors; and 3) both do not require prior restriction enzyme digestion of the nucleic acid, circumventing potentially troublesome RE/methylation systems.

Thus, Applicants' present invention overcomes these limitations in the prior art:, As noted above, the present invention discloses two methods of obtaining a biological molecule from recombinant microorganisms using environmental samples. First, protoplasts prepared directly from environmental sources, without prior culturing of the donor microorganisms are fused with recipient protoplasts, producing recombinant microorganisms. The second method of obtaining a biological molecule from a recombinant microorganism isolates nucleic acid directly from environmental sources, without prior culturing of the microorganisms. This isolated nucleic acid is encapsulated in donor liposomes and fused with recipient protoplasts, producing recombinant microorganisms.

In both methods of the present invention, the first step comprises obtaining an environmental sample having microorganisms, and any method of obtaining the sample is within the invention. The nucleic acid from these microorganisms can be isolated and inserted into donor liposomes, or donor protoplasts prepared, either of which is then fused with recipient protoplasts, producing recombinant microorganisms. A biological molecule is then recovered.

In the second method, the isolation of nucleic acid, both DNA and RNA, is based on methods well known in the art. Preferred methods are detailed in Examples 2 and 4. Methods of transcribing RNA into DNA utilize an enzyme called reverse-transcriptasie. Methods of reverse-transcription are well known in the art, and are detailed in Example 4. Similarly, preferred methods of preparing donor liposomes, fusing donor liposomes to recipient protoplasts, and selecting for recombinant microorganisms are detailed in Examples 3–6. In addition, preferred methods of preparing donor protoplasts, and fusing donor protoplasts to recipient protoplasts are set forth in Examples 7 and 8.

After a recombinant microorganism is selected, it is permitted to produce a biological molecule, using techniques standard in the art. Thereafter, the biological molecule produced is recovered. The biological molecule can be screened for numerous functions. The following descriptions of these potential functions are in no way an attempt to exclude other possible functions. The descriptions are designed only to be exemplary.

First, the biological molecule of the claimed invention may be used as a drug to treat human disease and cancer. Examples of these treatments are described below, although the descriptions are not meant to be limiting.

Biological molecules uncovered by the claimed invention may have new antiinfective activity, such as new antibiotics. In recent years, the incidence of infections by strains of pathogens, resistant to many, and occasionally all, commercial antibiotics has increased. Antibiotic resistance is identified by the World Health Organization (WHO,) as one of the most important medical problems facing world populations, and in response, the U.S. government established several initiatives encouraging industry to identify and commercialize new antibiotics.

The claimed invention could uncover new anti-infectives for Gram$^-$ bacteria, such as *Pseudomonas* and *E. coli*, both of which cause serious opportunistic or hospital-acquired infections, Gram$^+$ bacteria, such as *Enterococcus* and *Staphylococcus*, both of which cause respiratory and other infections, fungal pathogens, such as Candida, which presents serious infections in immune-compromised patients, and *Mycobacterium*, the cause of tuberculosis.

The claimed invention could also uncover new anticancer drugs. Cancer continues to be a major category of uncontrolled diseases, resulting in extensive morbidity and mortality worldwide. In the United States, more than 1,300,000 people are diagnosed with cancer each year, and approximately 500,000 people will die from cancer this year. Non-drug interventions, such as radiation therapy and surgery, remain the predominant method of treatment due to a general lack of effective drugs.

Many of the anticancer drugs that have shown efficacy against solid tumors are in fact derived from natural sources. For example, one of the most promising recent drugs for treating ovarian and breast cancer is Taxol, a drug obtained from a terrestrial plant called the yew tree. Other anticancer drugs are derived from microbial sources For instance, doxorubicin was first isolated from a *Streptomyces* species.

Of particular relevance to Applicants is the observation that, even though certain marine organisms live near the ocean surface and thus are exposed to constant ultraviolet (UV) radiation from the sun, a known cancer causing agent, these organisms do not develop cancer. The lack of cancer in these organisms may suggest the presence of protective or repair molecules, derived either from the organism itself or a symbiotic or associated microorganism, that may potentially act as anti-cancer drugs. Thus, the claimed invention could uncover these compounds.

The claimed invention could also uncover novel central nervous system (CNS) drugs. The two targeted categories of CNS drugs are (1) medications for neurodegenerative diseases, such as epilepsy, seizures, Parkinson's Disease, and for neuroprotection after stroke or head trauma, and (2) psychotherapeutics for treating diseases such as anxiety or schizophrenia. All of these diseases are complex, involving numerous receptor classes or receptor subtypes.

Receptors are large molecules, generally proteins, located in or on the cell surface membrane. Receptors receive a chemical signal through the binding of another molecule, called a ligand. Ligands include hormones, growth factors, neurotransmitters, etc., that circulate in varying concentrations and at varying times throughout the bloodstream.

The binding of a receptor to a ligand is highly specific, like a lock and key, and exists as the central means of cellular communications in the body. Because of this central role of receptors, more than one-half of all neurological drugs work by interacting either with the receptor or the ligand.

Enzymes are proteins which accelerate cellular information processing. While some receptors are also enzymes, most enzymes are found in the cascade of secondary events inside the cell, taking place after activation of a receptor. Enzymes amplify the signal sent by the receptor. Furthermore, some enzymes are activated (or inhibited) by multiple receptors. Thus, a biological molecule recovered by the claimed invention could act on a single enzyme or a single receptor and achieve far-reaching cellular effects. A biological molecule with such far-reaching cellular effects could be used to treat human disease.

For instance, a biological molecule recovered by the claimed invention may interact with receptors involved in a pathology of a neurological disease. For example, some degenerative diseases involve an overexcitation of nerve cells caused by agents binding to a class of receptors on nerve cells, called excitatory amino acid (EAA) receptors. During a stroke, these EAA receptors are overexcited allowing an influx of calcium ions into the cell through ion channels. This influx leads to malfunction or death of the nerve cells. Accordingly, the claimed biological molecule could be a potential therapy for neurological disease and stroke effects if the biological molecule interacts with the EAA receptors or ion channels.

Similarly, Parkinson's Disease might also be treated by biological molecules of the claimed invention acting on EAA receptors, dopamine (biogenic amine) receptors, or dopamine uptake sites. Psychotherapeutic diseases may also respond to products of the claimed invention acting on EAA receptors, at biogenic amine (serotonin) receptors, or inhibitory amino acid receptors, such as GABA receptors.

Furthermore, biological molecules produced by the claimed invention may either activate (as an "agonist") or inactivate (as an "antagonist") the receptors for, inter alia, insulin, tumor necrosis factor, growth factors (EGF, NGF, PDGF), interleukin-l, endothelin, and somatostatin. The claimed biological molecule may be used as an agonist or antagonist of these receptors.

Biological molecules recovered by the claimed invention may also be used for industrial purposes. For instance, products of the claimed invention could recover or remediate heavy metals, such as lead, mercury, chromium, arsenic, cadmium, copper, and gold. Lead is a major environmental health concern because of its adverse effects on mental development of children exposed to modest levels in drinking water or by contact with lead-based paints. Children with elevated lead levels in their blood are associated with significantly lower average IQ scores in a number of studies. Acute lead poisoning requires a course of hospital treatment to purge the body of lead. More than 12% of municipal water systems in the U.S. fail to meet minimum EPA standards of 15 ppm for levels of lead. Home well water in many regions and localities is also contaminated with lead. The claimed invention may allow for the identification and isolation of biological molecules that can potentially remediate lead and other heavy metals from contaminated water.

Similarly, the biological molecule produced by the claimed invention can aid in the removal of pollutants, such as phenolic and aromatic pollutants from industrial process waste streams. Phenols comprise pesticides and toxic pollutants formed as a by-product of a number of industrial processes, including pulp and paper production, plastics manufacture, and lumber (plywood) processing. Many of these processes require washing or cooling steps resulting in waste streams containing phenols.

Like lead, certain phenols have emerged as serious environmental health threats. Certain phenol derivatives, such as PCBs, for example, have an adverse effect on mental development (human children chronically exposed to PCBs present with reduced IQ scores) and on wildlife (egg viability decreased in birds exposed to PCBs). Other phenolic compounds may interfere with the immune and/or the reproductive systems of animals, by interacting with hormones and hormone receptors.

In addition, a biological molecule of the claimed invention can aid in the removal of biofilms generated by industrial waste. Presently, these biofilms are currently removed by environmentally damaging chemicals, leading to increasing regulation and banning of these chemicals. Biofilms can also contribute to serious public health threats by harboring harmful pathogenic microorganisms. For example, Legionnella, the microorganism responsible for Legionnaire's Disease, grows in or on biofilms in air conditioning cooling towers. Escape of this pathogen into air vent systems causes disease outbreaks and, frequently, deaths. Removal of biofilms by biological molecules produced by the claimed invention should reduce the likelihood of these outbreaks.

Furthermore, a biological molecule of the claimed invention may also be used as an industrial enzyme. For instance, thermostable enzymes, or products that provide resistance to high concentrations of heavy metals and salts, or to strong reducing agents, may be uncovered by the claimed invention.

Similarly, a biological molecule produced by the claimed invention may be utilized as biotechnology research products. For instance, enzymes that break down agarose, a material used in separating nucleic acid, may be produced by the claimed invention. Moreover, a biological molecule that can degrade protein will have widespread use in biotechnology.

Thus, as described above, the potential uses of a biological molecule produced by the claimed invention are numerous. One skilled in the art would be able to take the biological molecules produced by the claimed invention and screen for these and other potential uses.

The present invention also relates to a method of making recombinant microorganisms, wherein the method comprises obtaining an environmental sample having microorganisms. The nucleic acid from these microorganisms is isolated and inserted into donor liposomes or donor protoplasts are prepared. These donor liposomes or donor protoplasts are fused with recipient protoplasts, producing recombinant microorganisms. These recombinant microorganisms are selected.

The present invention also relates to processes of isolating or making a biological molecule, wherein the process comprises cloning the genetic material isolated by one of the above processes into a vector. Cells are transformed with the vector using standard techniques, and then cultured. A biological molecule is produced by the transformed cell and thereafter can be isolated using standard techniques.

The present invention also relates to a method of making a recombinant library, wherein the method comprises obtaining an environmental sample having microorganisms. The nucleic acid from these microorganisms is isolated and inserted into donor liposomes or donor protoplasts are prepared. These donor liposomes or donor protoplasts are fused with recipient protoplasts, producing recombinant microorganisms. The recombinant microorganisms are combined, producing a recombinant library.

The present invention also relates to the product of any of the above processes.

It will be apparent to those skilled in the art that various modification and variations can be made in the present invention without departing from the spirit or scope of the invention. Thus, it is intended that the present invention cover the modifications and variations of this invention provided they come within the scope of the appended claims and their equivalents.

For purposes of illustrating preferred embodiments of the present invention, the following, non-limiting examples are included. These results demonstrate the feasibility of recovering a biological molecule from a recombinant microorganism. It is, however, to be understood that the discussion also applies to methods of isolating, identifying, and making a biological molecule from a recombinant microorganism, as well as the products themselves. Furthermore, the claimed invention includes a method of making a recombinant microorganism and a recombinant library. Finally, the recombinant microorganism and the recombinant library are included in the claimed invention.

EXAMPLES

Example 1

Recipient Protoplast Formation a) Recipient Microorganisms. Three different strains of bacteria were used to produce recipient protoplasts. These strains have been optimized to increase the chances of obtaining recombinants. The first strain exists as a melanin-producing strain of *Bacillus subtilis*, which requires supplemental proline for growth. The selectable markers, proline synthesis and melanin pigment production, distinguish recombinant cells from possible background (e.g., from culturable bacterial contaminants which grew up on the selection plates).

The second strain used to produce recipient protoplasts was *Streptomyces lividans*, ATCC 35287. This strain also required supplemental proline and included a plasmid, encoding antibiotic resistance to thiostrepton and tyrosinase genes (plJ702.). This strain of bacteria preferentially obtained recombinants with non-culturable marine actinomycetes.

Members of the bacterial order Actinomycetales (of which Streptomyces is a member) produce more than 50% of the antibiotics described to date. (31) Recent studies show that *Streptomyces* comprise up to 5% of the indigenous bacterial population in marine sediments. (32) Nonculturable Actinomycetales are therefore an important target of the claimed invention by attempting to obtain genetic pathways producing novel antibiotics.

Actinomycetes are the main producers of a large and diverse family of clinically important antimicrobial agents, called polyketide antibiotics (7). Although these compounds are produced by a diverse array of biosynthetic enzymes, the genes of the enzymes at the beginning of each pathway, the ketosynthases, as well as the acyl carrier proteins, have highly conserved sequences. It is feasible to use oligonucleoticle probes complementary to these sequences for probing Actinomycetes recombinants in order to identify the presence of novel polyketide antibiotic genes in the recombinant microorganisms.

The third strain used to produce recipient protoplasts was *Streptomyces antibioticus*. This strain of bacteria lacks antibiotic resistance, requires proline for growth, and produces melanin as a scorable marker.

b) Cell-Culture Conditions of Bacteria Strains Prior to Protoplast Formation. *Streptomyces lividans* and *Streptomyces antibioticus* cultures were identically grown, plated and maintained on modified R2 YE media. (See appendix for description of solutions.) For protoplast formation, cells were inoculated into 100 mL YEME broth amended with 10 g sucrose (10%) and 0.5 g glycine (0.5%) to prevent mycelial clumping. These cultures were incubated at 27° C. for 48 h.

*Bacillus subtilis* was plated and maintained on modified nutrient agar. For protoplast formation, the cells were inoculated into 100 mL modified nutrient broth amended with 10 g sucrose (10%), and incubated at 27° C. for 48 h.

c) Recipient Protoplast Formation. *S. lividans* and *S. antibioticus* protoplasts were produced by the following procedure: 48 h cultures, 1 mL at approximately $1 \times 10^6$ cfus/ml, were divided into 2 equal aliquots, centrifuged at 1,100 x g for 10 min, resuspended in 25 mL of 10.3% sucrose solution, centrifuged for 10 min, and washed a second time in 10.3% sucrose. The supernatant was discarded and the cell pellet resuspended in 5 mL of medium P (a hypertonic solution which provides an osmotically stable environment for the protoplasts) containing lysozyme (1 mg/mL), followed by incubation for 80 min at 35° C. Protoplast formation was confirmed by phase-contrast microscopy. The protoplast pellet was washed 2X in medium P by centrifugation with gentle resuspension, and then resuspended in 20 mL of medium P and frozen "slowly" (33) in 1 mL aliquots at −70° C. Protoplast viability was determined by plating dilutions of the protoplast mixture on R2 YE medium supplemented with proline (100 μg/mL). At least 45% viability was obtained.

For *B. subtilis* protoplast formation, cells were centrifuged at 8,000 g for 10 min at 18° C., and resuspended in SMM buffer to an $A_{650}$ of 2.0. Lysozyme (in SMM buffer) was added to a final concentration of 100 g/ml, followed by incubation at 42° C. for 30 min. Protoplast formation was confirmed by phase-contrast microscopy. The protoplasts were centrifuged, and the pellet resuspended in ⅕ volume of SMMA buffer. Viable protoplasts were determined by plating dilutions of the protoplast mixture on RD regeneration medium; at least 80% protoplast viability was found for this strain.

Example 2

Isolation of DNA a) Sediments. The protocol for DNA isolation was as follows: 50 mL sediment cores were resuspended in 50 mL of 1 mM sodium phosphate buffer, pH 7.0 and 1.5 g of sodium dodecyl sulfate (SDS). The samples were incubated at 70° C. for 45 min with occasional mixing to lyse the cells in the samples, and centrifuged at 15,000 x g for 15 min to pellet insoluble solids. The supernatant was transferred to a clean centrifuge tube and the pellet washed once with 50 mL of 1% SDS in 1 mM phosphate buffer. All supernatants were pooled, incubated on ice for 30 min, mixed with solid potassium acetate to 0.5 M final concentration, further incubated on ice for 1 to 2 h, and centrifuged at 15,000 x g for 30 min. The supernatant was mixed with an equal volume of 2-propanol to precipitate the DNA and incubated overnight at 4° C. The precipitate was recovered by centrifugation at 15,000 x g for 30 min, and washed with 70% ethanol. The crude DNA pellet was dried in a lyophilizer and then dissolved in 25 mL of TE buffer, ethidium bromide was added to 0.6 mg/mL and ammonium acetate to 2.6 M final concentration, incubated in the dark for 10 min, extracted with an equal volume of Tris-saturated phenol:chloroform, and centrifuged at 15,000 x g for 10 min. The aqueous phase was then extracted with an equal volume of chloroform and centrifuged, the aqueous phase from this extraction was transferred to a clean centrifuge tube and the DNA precipitated by the addition of an equal volume of 2-propanol. The precipitated DNA was recovered and washed as described above, and the dry pellet redissolved in 3 mL of 0.3 M NaCl in TE and loaded into a 6–7 mL DEAE Sephadex column, washed with 20 mL of 0.3 M NaCl in TE, and eluted with 0.5 M NaCl in TE. The isolated DNA was precipitated, washed and dried as described above, and stored at −70° C.

b) Sea Water. The following procedure was used: Sea water samples containing nonculturable microorganisms were filtered through 10 $\mu$m pore-size filters to eliminate multicellular planktonic organisms. The filtered microorganisms were collected and concentrated using 0.2 $\mu$m pore-size filters. The cells were resuspended in 1 mL of 2X STE Buffer to a concentration of approximately $10^{10}$ cell/mL, and mixed with 1 mL of 1% molten low-melting-point agarose. The cell-containing agarose plug was placed in 10 mL of Lysis Buffer and incubated at 37° C. for 1 h. The agarose plug was then transferred to 40 mL of ESP Buffer, and incubated at 55° C. for 16 h. The solution was decanted, replaced with fresh ESP Buffer, and incubated at 55° C. for 1 h. The plug was placed in 50 mM EDTA and stored at 4° C. The plug was dialyzed against 20 mL of Buffer A (see Appendix) overnight. The buffer was replaced with 10 mL of Buffer A, incubated at 68° C. to melt the agarose, digested with gelase (agarase), gently extracted with phenol-chloroform to remove protein, the DNA precipitated with ethanol, pelleted, and washed it with 70% ethanol. The dried DNA pellet was stored at −70° C.

Example 3

Production of DNA-Loaded Liposomes

Lipofection-based DNA transfer technology is depicted schematically in FIG. 1. The following protocol was used for the production of liposomes. About 100 mg of egg phosphatidyl choline, 40 mg 7-dihydrocholesterol, and 10 mg stearylamine were dissolved in 5 mL of chloroform:methanol (2:1 vol/vol). One mL of the solution was placed in an 50 mL round-bottomed flask. The flask was attached to a rotary evaporator, evacuated, rotated at about 60 rpm, and immersed in a 30° C. waterbath. Once the liquid evaporated and a dry lipid film was deposited on the walls of the flask, the flask was kept for another 15 min under the conditions described above, then placed inside a lyophilizer jar and the last traces of organic solvent remove in the lyophilizer over 30 min. DNA (1–2 mg) was dissolved in 1 mL of Buffer G (see Appendix) and transferred into the flask containing the dry fatty acid film. The flask was attached to the evaporator, and rotated at room temperature and pressure at 60 rpm for 30–45 min. By then, all the lipid was removed from the wall of the flask, forming a milky white suspension of liposomes with DNA entrapped in them. The suspension was allowed to stand for 1 h at room temperature to complete the swelling process.

Example 4

Isolation and Reverse-Transcription of RNA

Due to the large number of reverse transcriptase (RT) inhibitors present in the environment, total RNA should be purified from whole cells.

Microorganisms can be obtained from seawater as described previously. For sediment samples, 10 g sediment would be homogenized in 90 ml 3% NaCl in a chilled Waring Blender 3x for 60 s, with cooling in ice between each run. The homogenate is then diluted to 500 ml and centrifuged for 15 min at 1,000 xg to pellet the sediment The supernatant (containing microorganisms removed from sediment particles) is set aside (4° C.), the sediment is homogenized again for 60 s, diluted and centrifuged as described. The supernatants of the low speed centrifugations are combined and centrifuged at 10,000 xg for 30 min to pellet down the microorganisms.

Resuspend cells in 0.5 ml of lysis buffer (50 mM Tris-HCl, 100 mM NaCl, 1% Sarkosyl, pH 8.0), freeze on dry ice, thaw and sonicate 2x for 10 sec each with a microtip sonicator at 30 W. Add 10 $\mu$g/ml protease K, incubate for 60 min at 37° C. add an equal volume of phenol/chloroform/isoamyl alcohol, microcentrifuge for 5 min and transfer the aqueous phase to a clean tube. Reextract with an equal volume of phenol/chloroform/isoamyl alcohol, then with an equal volume of chloroform/isoamyl alcohol, transfer aqueous phase to a new tube. Add 15 $\mu$l of 5 M NaCl and fill tube with ethanol, precipitate overnight at −20° C. Microcentrifuge for 15 min, dry pellet and redissolve in 95 $\mu$l DNase digestion buffer (20 mM HEPES, 5 mM $MgCl_2$, 1 mM $CaCl_2$, pH 7.5), add 4 $\mu$l of 2.5 mg/ml RNase-free DNase I, incubate for 60 min at 37° C., extract with phenol/chloroform/isoamyl alcohol, at 10 $\mu$l of 5 M NaCl and 600 $\mu$l of 100% ethanol to the aqueous phase and precipitate over night at −20° C. Microcentrifuge for 15 min, rinse with 70% ethanol, dry the pellet and redissolve in 100 $\mu$l of diethylpyrocarbamate (DEPC)-treated water and store at −70° C.

To remove RT inhibitors, add 10 $\mu$l of LiCl to 100 $\mu$l of RNA solution, allow the RNA to precipitate on ice for 2 hours, centrifuge at 15,000 xg for 20 min at 40° C., and redissolve in 100 $\mu$l DEPC-$H_2O$. Repeat LiCl precipitation, wash RNA pellet with 70%, ethanol 2x, and resuspend in 100 $\mu$l DEPC-$H_2O$.

RT reactions are carried out in a 20 $\mu$l final volume containing 5 $\mu$g total RNA, 2 $\mu$l 0.1 M dithiothreitol (DTT), 4 $\mu$l 5x RT-reaction buffer, 20 U RNase inhibitor, 300 ng of random decamers, 4 $\mu$l 5 mM dNTPs and 20 U of reverse transcriptase. The reaction is incubated in 37° C. for 2 hours, and terminated by incubation at 95° C. for 2 min. "Long" PCR amplifications are performed in a thermal cycler in a 40 $\mu$l final volume containing 2 $\mu$l of the RT reaction, 100 pmoles random primers, one U to Taq DNA polymerase, 2 $\mu$l 5 mM dNTPs, and 4 $\mu$l PCR buffer (75 mM Tris-HCl, pH 9.0, 20 mM $(NH_4)_2SO_4$, 0.01% Tween 20). The reaction is carried out for 40 cycles using the following conditions: 94° C. for 1 min (initial denaturation), 16 cycles of 30 s at 94° C. and 10 min at 66° C.; followed by 12 cycles of 94° C. and 10 min at 66° C., with 15 s incremental lengthening of the 66° C. step for each of the last 12 cycles; followed by a final 10 min extension at 72° C.

The amplified cDNA can be enclosed in liposomes as described previously. This procedure should yield DNA fragments of ≦6 kb.

Example 5

Liposome-Mediated Transformation a) Transformation of *S. lividans*. Nucleic acid loaded liposome and *S. lividans* protoplast suspensions were adjusted to have approximately the same turbidity, and equal volumes were mixed and protoplast/liposomes were sedimented at 3,000 rpm for 7 min in a benchtop centrifuge. The supernatant was decanted, the protoplast/liposome pellet resuspended and washed in 5 mL of medium P, the supernatant was discarded after centrifugation. The protoplast liposome pellet was dispersed by tapping, 0.8 mL of 50% PEG in P medium were added and the pellet immediately suspended by pipetting rapidly with a Pasteur pipette once. The suspension was incubated for 2 min at room temperature and aliquots plated in R2 YE agar without L-proline or on modified R2 medium.

Nine days after plating on R2 agar, recombinant colonies able to produce proline were observed growing at different rates on the plates. Spores from these colonies were inoculated again on R2 medium to ascertain that the proline auxotrophic mutation had been rescued by complementation of the recombinant DNA introduced during lipofection.

b) Transformation of *S. lividans* with Environmental Microorganism Actinomycin Pathway Genes. Chromosomal DNA was isolated from a sample containing an Actinomycete isolate known to synthesize an Actinomycin D analog. The DNA was encapsulated in liposomes as in Example 3, above, and fused with *S. lividans* protoplasts. The fusants were plated on R2YE agar containing actinomycin D (10 μg/mL) and incubated at 25° C. for 9 days.

Spores from lawns of actinomycin D resistant strains were collected and plated on R2YE agar without actinomycin D and incubated at 25° C. for 7 days. The agar was then extracted as in Example 11 and the extracts tested for antimicrobial activity against methicillin resistant *S. aureus* as in Example 13(a). Only one of the extracts was active and HPLC analysis indicated that the actinomycin D analog produced by the donor microorganism was not responsible for the observed activity.

c) Transformation of *B. subtilis*. Liposome and *B. subtilis* protoplast suspensions were adjusted to have approximately the same turbidity, equal volumes were mixed, and protoplast/liposomes were sedimented at 3,000 rpm for 7 min. in a benchtop centrifuge. The supernatant was decanted, the protoplast/liposome pellet resuspended and washed in 5 mL of SMMA, and the supernatant was discarded after centrifugation. The protoplast/liposome pellet was dispersed by tapping, 0.8 mL of 40% polyethylene glycol (PEG) 6000 (40% wt/vol in SMMA) was added, then shaken vigorously. After standing for 3 min at room temperature, samples were plated on nonselective recovery medium (this stabilizes the formation of diploids in *B. subtilis* and increases the frequency of subsequent genetic recombination (10)) and incubated at 37° C. for 48 hours. Colonies were reproduced in an identical arrangement on multiple plates, or replica plating, on selective recovery medium (RM1). After 3 to 5 days incubation at 30° C., melanin-producing, prototrophic recombinants were selected from the plates.

Example 6

Characterization of Lipofected Transformants

Transformants R1 and R2, selected from an experiment as in Example 5, using environmental samples from a sediment source taken from Cape Hatteras, N.C., were grown in broth and on plates using modified R2 medium without thiostrepton. After 7 days of incubation at 25° C., the cultures were harvested and extracted with equivalent volumes of 1:1 chloroform:methanol. The organic phase was collected and the solvent evaporated. The same procedure was followed for the *S. lividans* host. HPLC analysis of these extracts, performed according to Example 11, demonstrated substantial alteration in metabolite production and media utilization as indicated in FIGS. 4–7.

Example 7

Donor Protoplast Formation from a Variety of Microorganisms in an Environmental Sample Seawater and sediment samples containing nonculturable marine microorganisms were collected from a number of different geographic locations and marine environments. The seawater samples were concentrated, by centrifugation at 16,000xg for 20 minutes, and resuspended in protoplasting buffer (see Appendix). Since sedimentary microorganisms are attached to particulate material, these sediments were blended in a chilled Waring blender for 1 minute, then spun down at 2.000xg for 3 minutes to pellet the particulate material. The supernatant containing the microorganisms was centrifuged at 16,000xg for 20 minutes, and the cell pellet was resuspended in the protoplasting buffer.

In preparation for fusions between marine Actinomycetes and *S. antibioticus*, the cells were resuspended in an equal volume of medium P containing lysozyme (4 to 8 mg/ml), and incubated as described in Example 1c. Protoplast formation was confirmed by phase-contrast microscopy. The protoplasts were then washed 2X in medium P by centrifugation and gentle resuspension.

The marine protoplast preparations were monitored constantly to detect excessive cell lysis, in which case, the osmolarity of the protoplasting buffer(s) was increased with sucrose.

Several protoplast formation protocols call for the addition of DNase to the protoplasting buffer as a precautionary measure to eliminate the possibility that DNA-mediated transformation or transfection (from lysed cells) might occur. (10) Since the aim of the current invention was to recover the largest amount of genetic material from an environmental sample, this enzyme is not included in the buffers used in the present invention, and represents an important distinction between the current invention and the prior art. Given that the media is not optimized for the recovery of recombinant microorganisms, few viable cells are found growing on the recovery media after the fusions.

Fusions between donor protoplasts and heat-killed, or ultraviolet (UV)-inactivated, protoplasts have been successfully used for the production of new genotypes of industrial microorganisms. (11) However, the procedures described here represent substantial improvements over the existing protocols (10) and represent the best experimental approach.

These procedures can be further modified as dictated by the potential variables, indicated below, and are within the scope of the current invention.

Depending on the type of microorganism targeted in the environmental sample, different protocols must be used in preparing donor protoplasts. To produce protoplasts from Gram+ bacteria, after centrifugation, the cell pellet requires treatment only with lysozyme. In contrast, for Gram− bacteria, not only must the peptidoglycan cell wall be digested to produce spheroplasts, but the elimination of the outer membrane and conversion to true protoplasts may be required. To achieve this after centrifugation, the cell pellets were treated with lysozyme in EDTA.

a) Gram− Microbial Protoplast and Spheroplasts Formation. Gram− bacteria often, form structures called spheroplasts, and for the purpose of this application, are equivalent to protoplasts. Cell pellet (donor cells) from broth or plate culture was resuspended in SMM buffer to an $A_{650}$) of approximately 1.5, lysozyme (in SMM buffer) was added to a final concentration of 4 to 8 mg/ml, and the mixture incubated at 30° C., for an extended period of time (1 to 4 h). Protoplast formation was monitored by taking aliquots every 15 min and evaluating the samples by phase-contrast microscopy. The extended monitoring time was necessary due to the heterogeneous population of organisms derived from the marine samples, and the possible recalcitrance to degradation of the cell wall of these microbes. The resultant protoplasts were then centrifuged, and the pellet resuspended in ⅕ volume of SMMA buffer.

b) Gram+ Microbial Protoplast Formation. Cell pellets from broth or plate cultures were resuspended in SMM buffer amended with EDTA (25 mM) to an $A_{650}$ of approximately 1.5, lysozyme (in SMM buffer) was added to a final concentration of 4 to 8 mg/ml, and the mixture incubated at 30° C. for an extended period of time (1 to 4 h). Protoplast formation was monitored by taking aliquots every 15 min and evaluating them by phase-contrast microscopy. The resultant protoplasts were then centrifuged, and the pellet resuspended in ⅕ volume of SMMA buffer.

c) Alternative Procedures to Form Protoplasts from Certain Environmental Microorganisms. Some environmental microorganisms can be recalcitrant to formation of protoplasts using the above protocols. This may be due to cations or other molecules binding to the cell wall or to the presence of exopolysaccharide capsules. When recalcitrance was observed, the cell pellet was resuspended in a 3% NaCl, 10 mM EDTA solution and agitated in a Waring blender for 1 min. at 4° C., followed by centrifugation. The cell pellet was then used for protoplast generation as described previously. The EDTA chelates away divalent cations and the blending shears away the polysaccharide capsules. This approach has been used for the removal of polysaccharide capsules from marine bacteria with little observed cell lysis (34). Furthermore, cellulose, alginase, and βD-glucanase (5 mg/ml each) may be used in conjunction with lysozyme in the protoplasting buffer to help digest recalcitrant exopolysaccharides.

Example 8

Protoplast Fusions

Figure 2:
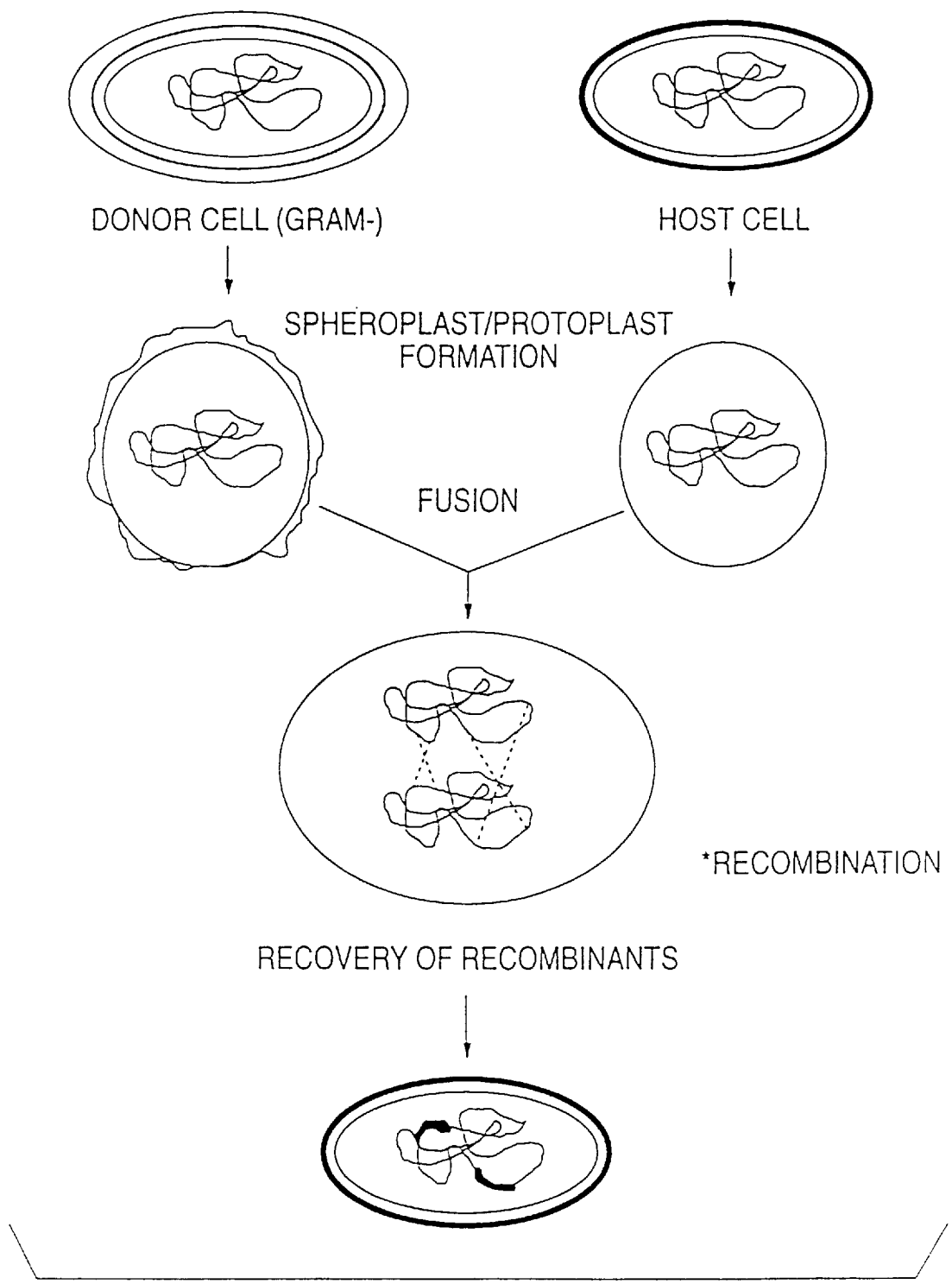
FIG. 2: Diagram of protoplast fusion-based DNA transfer Gram$^-$ donor cells.
Figure 3:
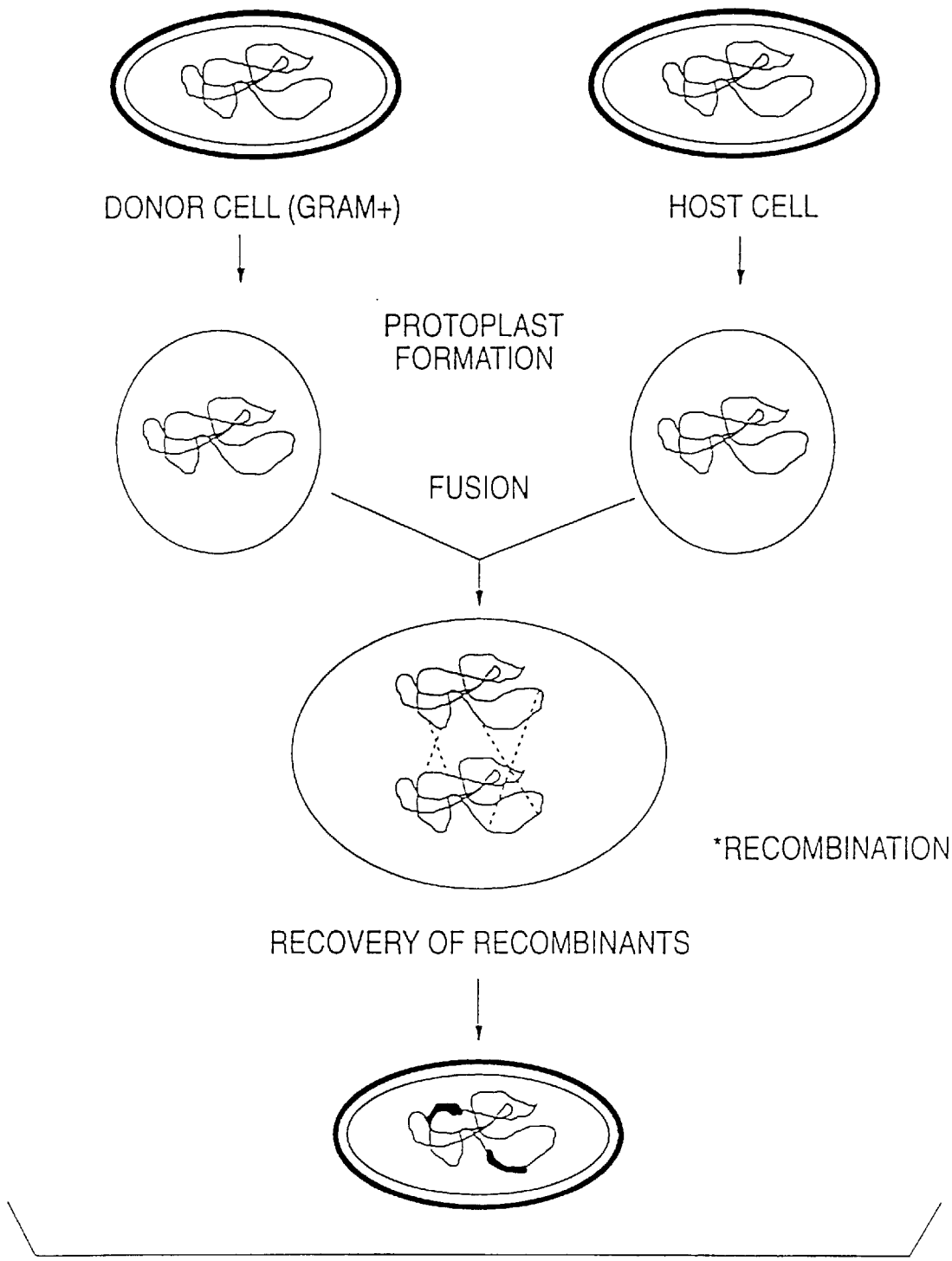
FIG. 3: Diagram of protoplast fusion-based DNA transfer Gram$^+$ donor cells.
Figure 4:
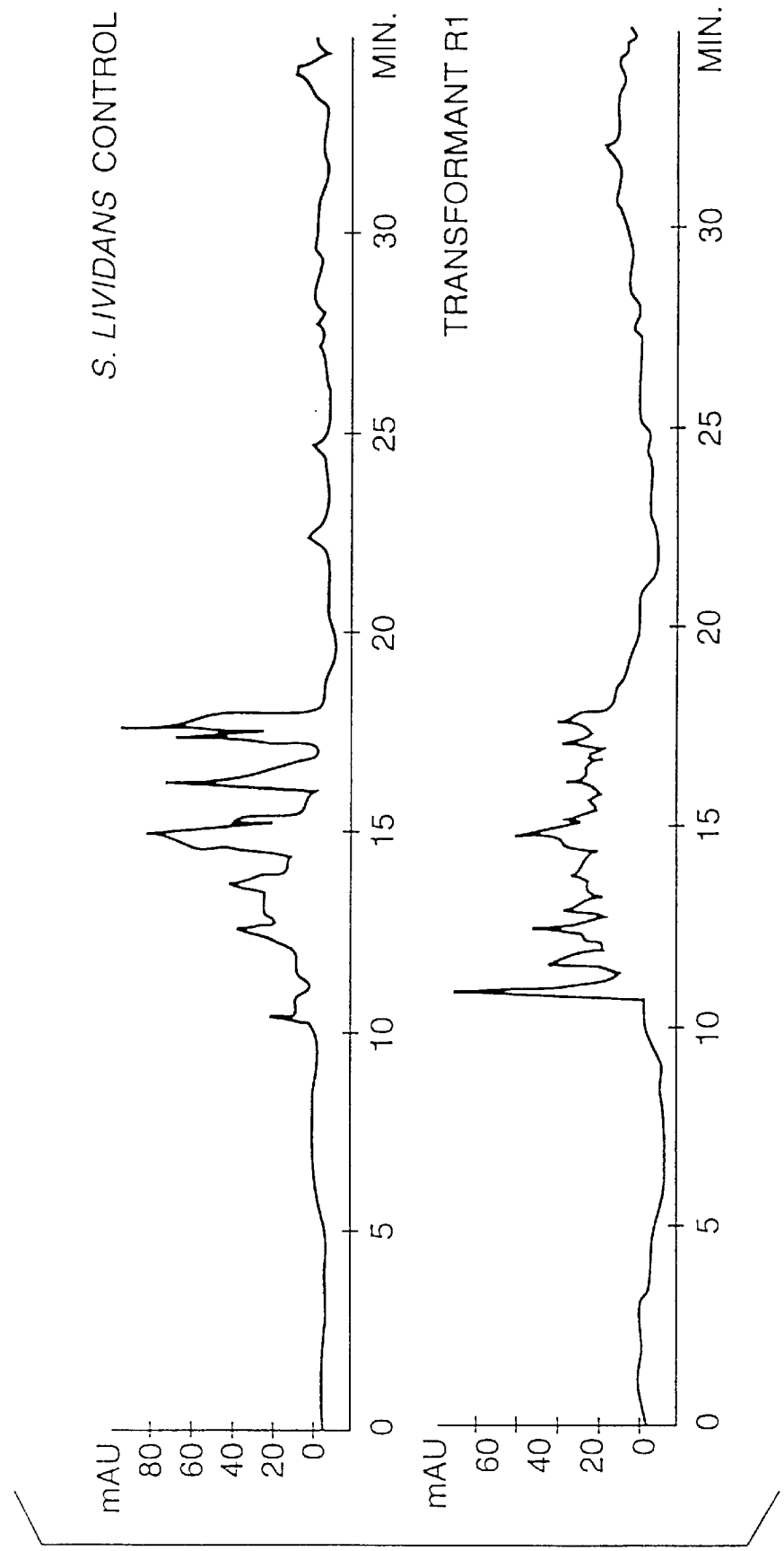
FIG. 4: Metabolite profile comparison between transformant R1 and *S. lividans* host grown on solid media.
Figure 5:
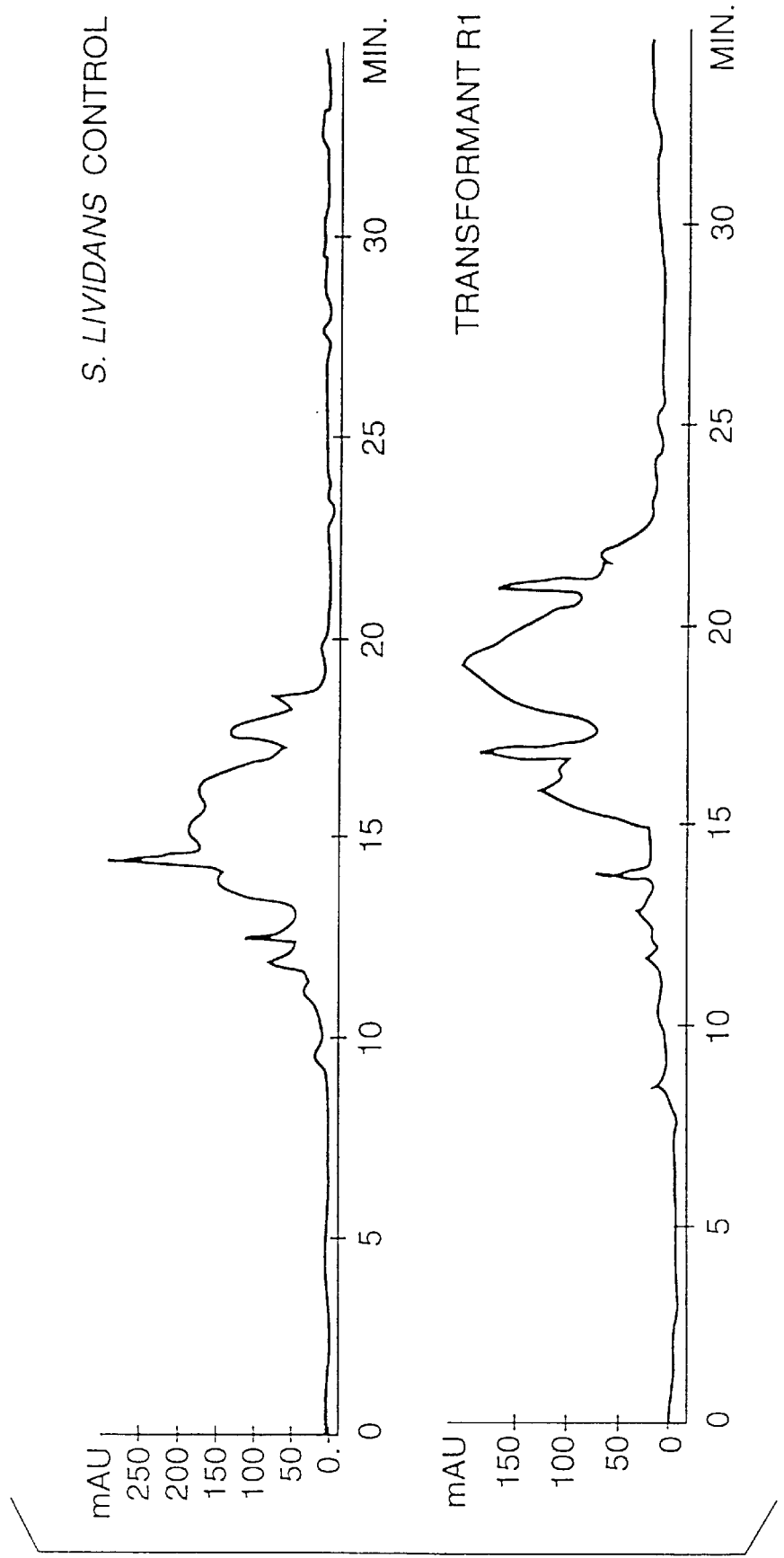
FIG. 5: Metabolite profile comparison between transformant R1 and *S. lividans* host grown on liquid media.
Figure 6:
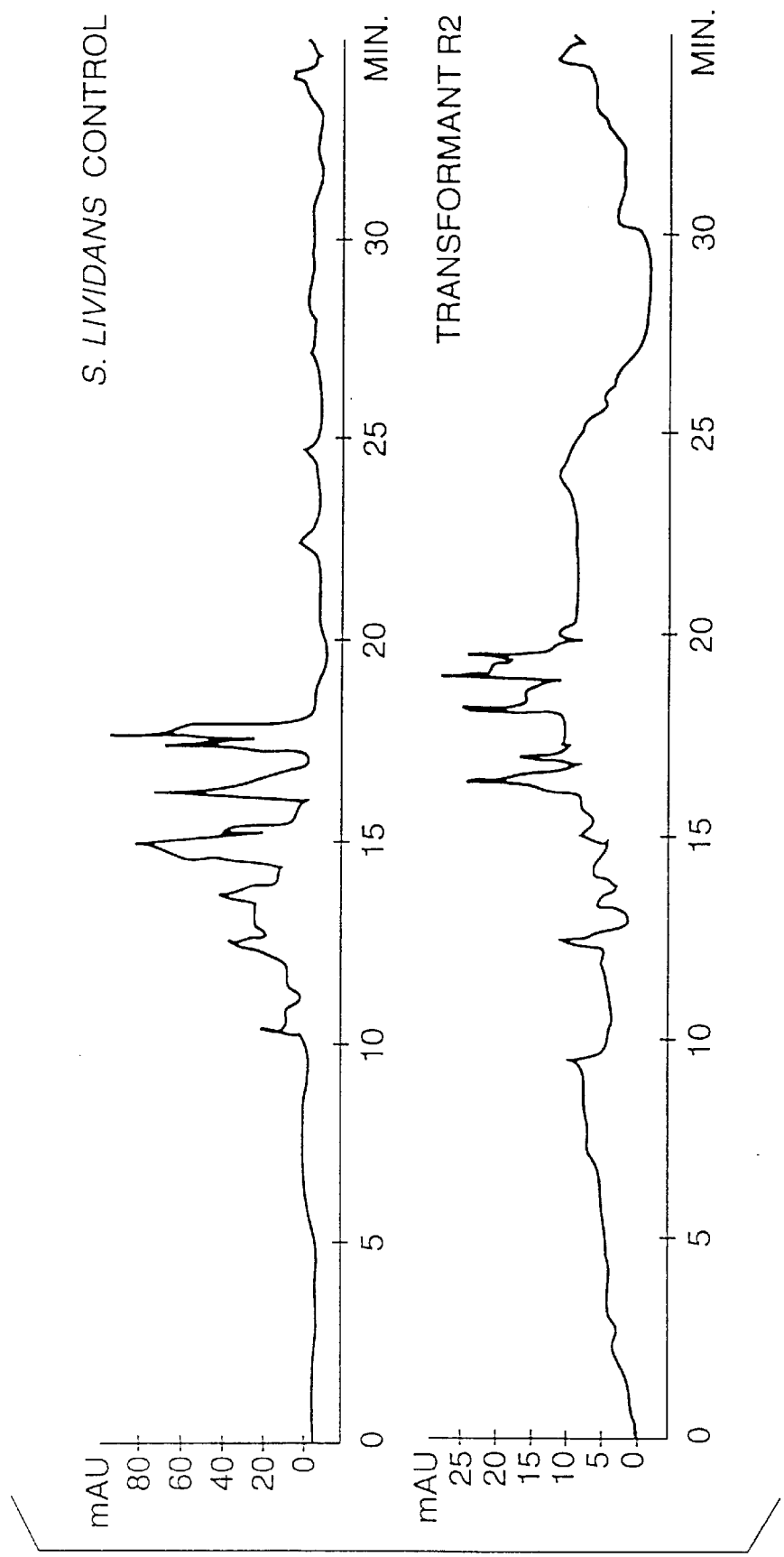
FIG. 6: Metabolite profile comparison between transformant R2 and *S. lividans* host grown on solid media.
Figure 7:
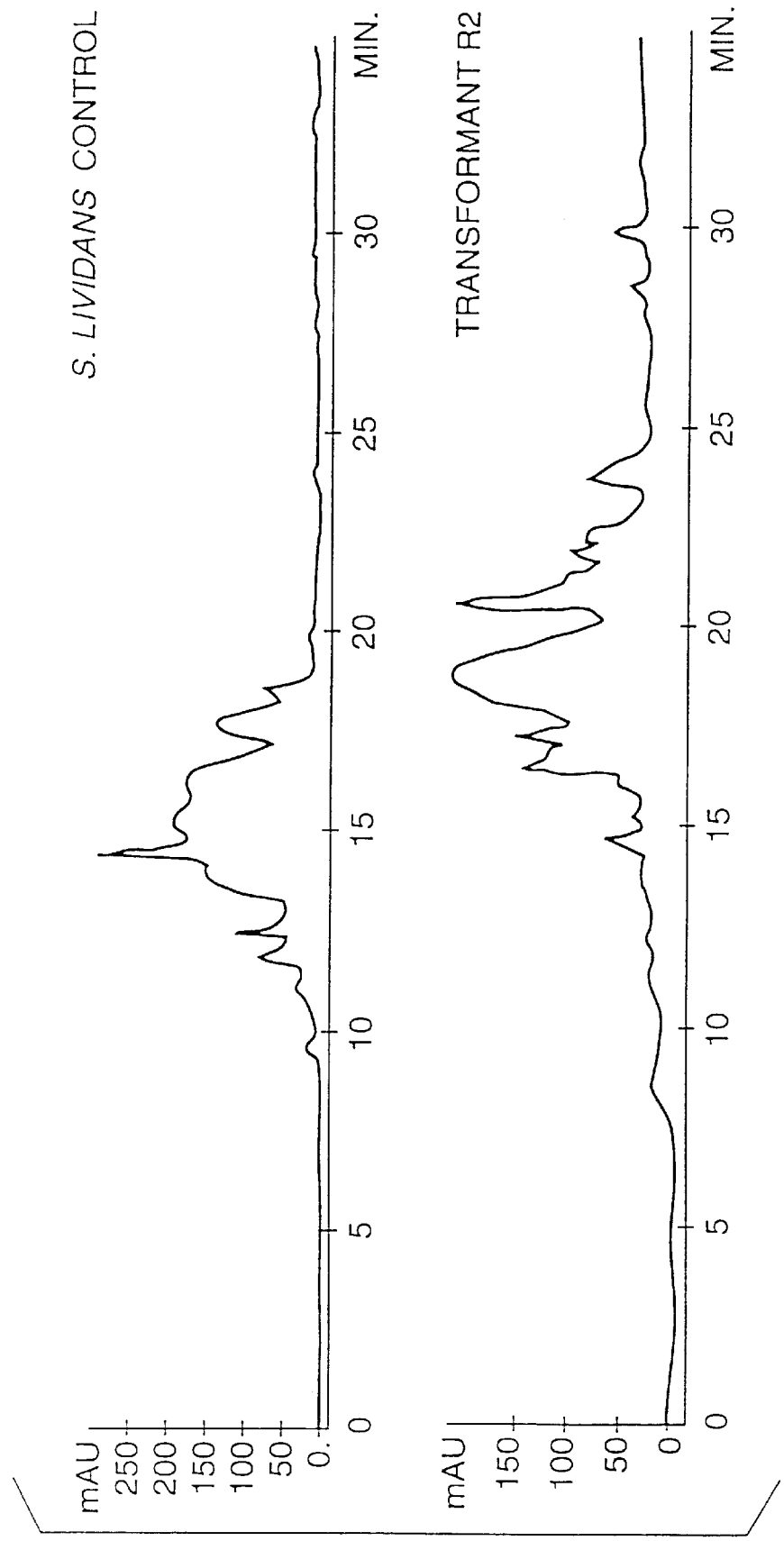
FIG. 7: Metabolite profile comparison between transformant R2 and *S. lividans* host grown on liquid media.

Protoplast fusion is depicted schematically in FIGS. 2 and 3.

a) *B. subtilis*. Equal volumes of the protoplast suspensions to be fused were mixed, 100 μL of the mixture was added to 900 μL of 40% polyethylene glycol (PEG) 6000 (40% wt/vol in SMMA), then shaken vigorously. After standing for 3 min at room temperature, samples were plated on nonselective recovery medium (see Appendix) (this stabilized the formation of diploids in *B. subtilis* and increased the frequency of subsequent genetic recombination (10)) and incubated at 37° C. for 48 hours. Colonies were replica plated on selective recovery medium (RM1). After incubation at 30° C., for 3 to 5 days, melanin-producing prototrophic recombinants were selected from the plates.

b) *S. antibioticus*. 500 μl of each of the two protoplast solutions to be fused were placed in a sterile centrifuge tube and spun down at 1,100 xg for 8 min. The supernatant was decanted, the protoplast pellet resuspended in 100 μl of medium P, and 900 μl of 50% PEG 1000 added (50% wt/vol in medium P). The protoplast-PEG suspension was mixed gently, incubated at room temperature for 1 min, diluted in medium P and added to RM2 modified soft agar overlays (46° C.), then mixed again and plated on RM2 plates. After 4 to 8 days incubation at 30° C., melanin-producing, prototrophic recombinants were selected from the plates.

Example 9

Culture of Recombinants

Recombinant strains were picked from plates and inoculated into 2–5 ml starter culture tubes. These samples were grown for various times (18 to 48 hr) to 0.5–1.0 O.D. and then used to inoculate 30–50 mL seed flasks. Again, after growth to 0.5–1.0 O.D., these cultures were used to inoculate replicate 300 mL working volume shaker flasks. These large cultures were incubated for up to 14 days. Broth samples were aseptically taken from these shaker flasks at selected time points for bioassay, biomass production measurements, viable cell counts and microscopic examination. As controls the host strains were cultured in media containing proline, and subjected to the same procedures as the recombinants.

Example 10

Extract Preparation. Method 1

Whole broth samples were centrifuged at 15,000 xg to coarsely separate biomass and broth insolubles from the supernatant culture solubles. The cell pellet was washed twice with one-tenth volume of sterile-filtered fresh media. Culture solubles and cell washes were combined and filtered through a 0.2 μ filter to remove all insolubles. Filtered culture fluid was partitioned into three 25 mL aliquots and placed into tared 50 mL centrifuge tubes, shell-frozen at −78° C. then freeze-dried for 24 h. Culture fluid insolubles and the cell pellet were combined, resuspended in 30 mL of deionized sterile water, partitioned into three 10 mL aliquots into tared 50 mL centrifuge tubes, frozen at −85° C. and freeze-dried for 24 h. Similarly, fresh medium was partitioned into three 25 mL aliquots placed into tared 50 mL centrifuge tubes, shell frozen and freeze-dried for 24 h to serve as a set of control samples. One set of dried solids (culture supernatant, medium, cells/broth insolubles separately) was resuspended via sonication or a rotor-stator homogenizer in methylene chloride-methanol mixture (9:1 v/v) at a rate of 5 mL of solvent mixture per 0.2 gram of solids. The amount of used solids was adjusted so that no more than 15 mL of solvent was used per extraction. Resuspended samples were shaken at 4° C. for 24 h then filtered through solvent resistant membrane filters to separate the nonpolar solvent solubles from polar/insolubles. The filtrate was evaporated under a stream of dry nitrogen (with vapor recovery) and the residue stored at −85° C. until assayed. The insoluble fraction is dried, resuspended in 15 mL of ethyl acetate, shaken at 4° C. for 24 h then filtered. The filtrate was evaporated under a stream of dry nitrogen (with vapor recovery) and the residue stored at −85° C. until assayed. The remaining insolubles were dried, resuspended in 15 mL of sterile water, shaken at 4° C. for 24 h then filtered. The filtrate was shell frozen and freeze-dried for 24 h.

Example 11

Extract Preparation. Method 2

Whole culture broth or minced Petri plate cultures with the solid agar media were extracted with equivalent volumes of 1:1 chloroform:methanol, the organic phase collected, and the solvent evaporated as in Example 10. Solid residues were prepared for assay as in Example 12 or were analyzed for metabolite profiles by HPLC using a C-18 reversed phase column and a linear solvent gradient from 75% water-25% methanol to 100% methanol over 35 min.

Extracts from the prototrophic transformants R1 and R2 obtained in these experiments displayed a metabolite profile different from those of *S. lividans*, as demonstrated by HPLC chromatograms (FIGS. 4, 5, 6, and 7). The altered profiles indicate that the introduction of the marine bacterial DNA yielded the production of new metabolites.

Lipofection experiments carried out with DNA isolated from a sample known to contain a marine Actinomycete that produces an actinomycin D type antibiotic resulted in the production of actinomycin D resistant transformants that also produced antibiotic(s) active against methicillin resistant *S. aureus*. Further evaluation of these transformants revealed that the active component in an organic solvent extract of a pooled culture of all the resistant organisms and their growth medium demonstrated a spectrum of antimicrobial activity against methicillin resistant *S. aureus* and a number of other test strains that was different from that of the antibiotic produced by the initial donor microorganism. HPLC analysis of this active material demonstrated further that the active component was not identical with that produced by the donor.

Example 12

Sample Preparation for Drug Discovery Assays

Dried samples of aqueous soluble material were solubilized in deionized water.

If necessary, a small amount of base or acid (1 M Tris base or Tris HCl) was added to achieve solutions having a pH of 6–8 to complete the solubilization of the extract. In the latter instance, the order of addition was acid, and when this was not successful, then base, at twice the volume of acid that was added. The sample was diluted to final volume of approximately 2 mL, using deionized water as described below.

Dried samples of material obtained using organic extraction methods were solubilized by the addition of 100% DMSO and dilution of the sample to final volume with a suitable amount of deionized water. If necessary a small amount of base or acid (1 M Tris base or Tris HCl) was added to achieve a solution having a pH of 6–8, or to complete the solubilization of the extract. In the latter instance, the order of addition was acid, and when this was not successful, then base at twice the volume of acid that was added.

Each sample was solubilized in a final volume sufficient to yield a solution of 1000 μg of material/mL and initial testing for biological activity was performed using a final concentration of 100 μg/mL of sample extract in individual assays.

Extracts from the host strain cultures were also tested to demonstrate that the host strains are not the source of bioactive metabolites.

Example 13

Tests for Bioactivity of Pharmaceutical Relevance a) Antimicrobial assays. Disc diffusion assays were carried out, and results interpreted, following the guidelines established by the National Committee for Clinical Laboratory Standards (NCCLS) for antimicrobial susceptibility testing (35). Mid-log cultures of test organisms were streaked over the entire surface of the appropriate agar plate. Blank paper discs (¼ inch diameter) saturated with solutions of test extracts were placed on these plates and incubated at a suitable temperature for the growth of the test organism. The test organisms used were: Gram positives, *Staphylococcus aureus, Enterococcus faecalis*, and *Bacillus subtilis*, Gram negatives, *Pseudomonas aeruginosa* and *Klebsiella pneumoniae*; anaerobes, *Bacteroides fragilis*; fungi, *Candida albicans* and *Saccharomyces cereviseae*. After incubation, the plates were examined, and zones of complete inhibition measured. The Minimum Inhibitory Concentration (MIC) was subsequently determined for the active metabolites.

b) Receptor assays. The radioreceptor-ligand based receptor assays used for the identification of recombinants producing compounds active at central nervous system receptors were: Adenosine receptor, α-adrenergic receptor, β-ardrenergic receptor, serotonin receptor, muscarinic receptor, and dopamine receptor. These assays were selected because they are good general indicators of bioactivity, and since these nonselective receptor assays can indicate activity at multiple receptor subtypes.

c) Cellular Functional Assays Once a biological molecule exhibits positive activity to a particular molecular target, the functional activity of the molecule must be determined. This process comprises of whether or not the compound activates (an "agonist") or inhibits (an "antagonist") the targeted receptor. Depending on the receptor and associated therapeutic goal, either agonist or antagonist activity will be sought.

All mentioned publications are hereby incorporated in their entirety by reference.

While the foregoing invention has been described in some detail for purposes of clarity and understanding, it will be appreciated by one skilled in the art from reading of this disclosure that various changes in form and detail can be made without departing from the true scope of the invention.

APPENDIX

General Experimental Procedures and Materials

Buffers and media—The following buffers and media were used in the experimental procedures described in the Examples.

Trace element solution—40 mg $ZnCl_2$, 200 mg $FeCl_3 \cdot 6H_2O$, 10 mg $CuCl_2 \cdot 2H_2O$, 10 mg $MgCl_2 \cdot 6H_2O$, $MnCl_2 \cdot 4H_2O$, 10 mg $Na_2B_4O_7 \cdot 10H_2O$, and 10 mg $(NH_4)_6Mo_7O_{24} \cdot 4H_2O$ were dissolved in 1 L d $H_2O$ and the solution filter sterilized.

Modified R2 YE medium—103 g sucrose, 0.25 g $K_2SO_4$, 10.12 g $MgCl_2 \cdot 6H_2O$, 10 g glucose, 0.9 g tyrosine, and 0.1 g Casamino acids (Difco 0230) were dissolved in 800 mL dH$_2$O, and 17 g agar added and the mixture was heat sterilized by autoclaving. Exactly 0.05 g KH$_2$PO$_4$, 2.95 g L-proline, 5.73 g N-tris(hydroxymethyl)methyl-2-aminoethanoesulfonic acid (TES), 0.2 g NaOH, and 5 g yeast extract were dissolved in 200 mL dH$_2$O, 2 mL of trace element solution added, and the pH adjusted to 7.2. The solution was filter sterilized and added aseptically to the autoclaved medium. To this solution was added aseptically 10 mL of 36% CaCl$_2$ and 50 mg of thiostrepton. The resulting solution was mixed and poured onto Petri plates.

Modified R2 agar—Same as Modified R2 YE Medium above, but no L-proline, Casamino acids or yeast extract were added.

YEME broth—3 g yeast extract, 3 g malt extract, 5 g Bacto Peptone, 10 g glucose, and 10 g NaCl, were dissolved in 1 L dH$_2$O and the solution heat sterilized by autoclaving.

TE buffer—10 mM Tris-HCl, pH 8.0, 1 mM EDTA. This solution was heat sterilized by autoclaving.

ESP buffer—1% Sarcosyl, 1 mg/mL proteinase K and 0.5 M EDTA.

Buffer A—100 mM NaCl, 10 mM Tris, pH 7.0 and 100 µg/mL acetylated bovine serum albumin.

Buffer G—0.015 M NaCl, 0.0015 M sodium citrate, 0.28 M sucrose, 0.001 M CaCl$_2$, and 0.1 M threonine.

STE buffer—1 M NaCl, 0.1 M EDTA, 10 mM Tris, pH 8.0.

Lysis buffer—10 mM Tris, pH 8.0, 50 mM NaCl, 0.1 M EDTA, 1% Sarcosyl, 0.2% sodium deoxycholate, and 1 mg/mL lysozyme.

Medium P—To 103 g sucrose, 0.25 g K$_2$SO$_4$, 2.03 g MgCl$_2$.6H$_2$O, dH$_2$O were added to 700 mL, and the mixture heat sterilized by autoclaving. The following stock solutions were filter sterilized: 0.5 g/L KH$_2$PO$_4$, 27.8 g/L CaCl$_2$.2H$_2$O, and 0.25 M N-tris (hydroxymethyl)methyl-2-aminoethanesulfonic acid (TES) (pH 7.2). Exactly 100 ml of each stock solution was added to the 700 mL base solution.

Hypertonic Nutrient Broth (HNB)—Per liter: 8.0 g Nutrient Broth (Difco), 1.0 g KCl, 0.25 g MgSO$_4$.7H$_2$O, 0.002 g MnCl$_2$.4H$_2$O, 0.025 g proline (25 µg/ml). Adjust pH to 7.0, autoclave, add filter-sterilized solutions of CaCl$_2$.2H$_2$O and FeSO$_4$.7H$_2$O to 5×10$^{-4}$ M and 1×10$^{-6}$ M, respectively, and sucrose to 0.5 M.

Modified Nutrient Broth/Agar (HNB/A)—Per liter: 8.0 g Nutrient Broth (Difco), 1.0 KCl, 0.25 g MgSO$_4$.7H$_2$O, 0.002 g MnCl$_2$.4H$_2$O. Adjust pH to 7.0, autoclave, add filter-sterilized solutions of CaCl$_2$.2H$_2$O and FeSO$_4$.7H$_2$O to 5×10$^{-4}$ M and 1×10$^{-6}$ M, respectively. For solid media, add 17 g of agar.

Sucrose maleate magnesium (SMM)—0.02 M maleate buffer (pH 6.5), 0.5 M sucrose, and 20 mM MgCl$_2$.

SMMA—SMM containing 1% Bovine Serum Albumin (BSA).

Regeneration Medium (RD)—Per liter: 1.0 g NH$_4$NO$_3$, 3.5 g K$_2$HPO$_4$, 1.5 g KH$_2$PO$_4$, 15 g agar, 81 g sodium succinate (0.33 M, pH 7.3), 5.0 g gelatin, 4.07 g MgCl$_2$.6H$_2$O, and 5.0 g glucose.

Recovery Medium 1 (RMI)—Per liter: 2.0 g NH$_4$NO$_3$, 14 g K$_2$HPO$_4$, 6.0 g KH$_2$PO$_4$, 15 g agar, 1.0 g sodium citrate, 0.2 g MgSO$_4$.7H$_2$O, 0.0025 g L-glutamate, 0.005 g L-lysine, 0.0125 g L-asparagine, 0.0025 g L-valine, 0.91 g tyrosine, 0.005 g MnCl$_2$.4H$_2$O, 0.024 g MgCl$_2$. 0.017 g CaCl$_2$, and 0.004 g FeSO$_4$.

What is claimed:

1. A method of producing a biological molecule from a recombinant microorganism, wherein the recombinant microorganism is produced by a method comprising:
   (a) obtaining an environmental sample having microorganisms;
   (b) preparing donor protoplasts from the environmental sample;
   (c) providing recipient protoplasts;
   (e) fusing said donor protoplasts with said recipient protoplasts to produce a recombinant microorganism, wherein the recombinant microorganism produces a biological molecule; and
   (f) recovering or isolating the biological molecule.

2. The method of claim 1, wherein the biological molecule is recovered.

3. The method of claim 1, wherein the biological molecule is isolated.

4. The method of claim 1 further comprising the step of identifying the biological molecule.

5. The method of claim 1, wherein the microorganisms from the environmental sample are selected from the group consisting of Gram positive bacteria, Actinomycetales, Archaea, or Gram negative bacteria.

6. The method of claim 1, wherein the environmental sample is obtained from a body of water.

7. The method of claim 6, wherein the body of water is an ocean.

8. The method of claim 1, wherein the environmental sample is obtained from sediment associated with a body of water.

9. The method of claim 1, wherein the environmental sample is obtained from soil.

10. The method of claim 1, wherein the environmental sample is obtained from air.

11. The method of claim 1, wherein the recipient protoplasts are derived from microorganisms selected from the group consisting of Gram positive bacteria, Actinomycetales, Archaea, Gram negative bacteria, fungi, or yeast.

12. A method of making a recombinant microorganism, wherein the method comprises:
   (a) obtaining an environmental sample having microorganisms;
   (b) preparing donor protoplasts from the environmental sample;
   (c) providing recipient protoplasts;
   (d) fusing said donor protoplasts with recipient protoplasts to produce a recombinant microorganism; and
   (e) selecting for said recombinant microorganism.

13. The method of claim 12, further comprising the step of combining all recombinant microorganisms produced by the fusion of the donor protoplasts with the recipient protoplasts to produce a recombinant library.

14. The recombinant library produced by the method of claim 13.

* * * * *